US006368845B1

(12) United States Patent
Ario et al.

(10) Patent No.: US 6,368,845 B1
(45) Date of Patent: *Apr. 9, 2002

(54) POLYPEPTIDES HAVING L-ASPARAGINASE ACTIVITY

(75) Inventors: Takeshi Ario; Madoka Taniai; Kozo Yamamoto; Masashi Kurimoto, all of Okayama (JP)

(73) Assignee: Kabushiki Kaisha Hayashibara Seibutsu Kagaku Kenkyujo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/635,705

(22) Filed: Aug. 9, 2000

Related U.S. Application Data

(60) Continuation of application No. 09/195,666, filed on Nov. 19, 1998, now Pat. No. 6,140,101, which is a division of application No. 08/869,927, filed on Jun. 5, 1997, now abandoned.

(30) Foreign Application Priority Data

Jun. 7, 1996 (JP) ............................................. 8-168172

(51) Int. Cl.[7] ............................. C07H 21/04; C12N 9/82
(52) U.S. Cl. .................. 435/229; 435/325; 435/252.33; 435/320.1; 536/23.1; 536/23.2; 536/23.5
(58) Field of Search ............................... 536/23.2, 23.5; 435/229, 252–33, 320.1, 325

(56) References Cited

FOREIGN PATENT DOCUMENTS

| EP | 0 726 313 | 8/1996 |
| JP | 119082/79 | 9/1979 |
| JP | 19018/80 | 2/1980 |
| JP | 04320684/92 | 11/1992 |

OTHER PUBLICATIONS

Ausubel et al. (Eds.), *Current Protocols in Molecular Biology*, vol. 1, John Wiley & Sons, Inc. (1995), pp. iii–xi; 9.0.1–9.0.3; 9.2.1–9.2.6.
Broome, J.D., Evidence that the L–Asparaginase Activity of Guinea Pig Serum is responsible for its Antilymphoma Effects, *Nature* 191:1114 (1961).
Harmes et al, A catalytic role for threonine–12 of *E. coli* asparaginase II as established by site–directed mutagenesis, *FEBS* 285(1):55–58 (1991).

Hay et al (Eds.), *ATTC Cell Lines and Hybridomas*, 8th Ed., American Type Culture Collection, Rockville, MD; pp. ii, iv, 150, 152, 159 (1994).
Horton et al, "Gene Splicing by Overlap Extension", *Methods in Enzymology*, 217:270–279 (1993).
Kidd, J. G., "Regression of Transplanted Lymphomas Induced in Vivo by Means of Normal Guinea Pig Serum", *The Journal of Experimental Medicine* 98:565:583 (1953).
Kozak, M., "An analysis of 5'–noncoding sequences from 699 vertebrate messenger RNAs", *Nucleic Acids Research* 15(20):8125–8148 (1987).
Laemmli, U.K., "Cleavage of Structural Proteins during the Assembly of the Head of Bacteriophage T4", *Nature* 227:680–685 (1970).
Sambrook et al, *Molecular Cloning: A Laboratory Manual*, Cold Spring Harbor Laboratory Press, (Cold Spring Harbor, NY, 1989), pp. xi–xxxviii.
Muramatsu, M., Labomanual Idenshi–Kogaku (Laboratory Manual for Genetic Engineering) (Maruzen Col, Ltd., Tokyo, Japan, 1988); Table of Contents.
Stern et al, "Construction of a Novel Oncogene Based on Synthetic Sequences Encoding Epidermal Growth Factor", *Science* 235:321–324 (1987).
Towbin et al, "Electrophoretic transfer of proteins from polyacrylamide gels to nitrocellulose shets: Procedure and some applications", *PNAS, USA* 76(9):4350–4354 (1979).
Yellin et al, "Purification and Properties of Guinea Pig Serum Asparaginase", *Biochemistry* 5(5):1605–1612 (1966).
Japan Pharmaceutical Excipients Council, Iyakuhin–Tenkabutsu (The Dictionary of Pharmaceutical Excipients) (Yakujinippo Ltd., Tokyo Japan, 1994); Table of Contents.
Japan Pharmaceutical Excipients Council, Iyakuhin–Tenkabutsu–Jiten–Tsuiho 1995 (Supplement for the Dictionary of Pharmaceutical Excipients) (Yakujinippo Ltd., Tokyo, Japan, 1995); Table of Contents.
Patent Abstracts of Japan, vol. 17, No. 158 (c–1041) (1993): abstract of JP 04 320684 of Nov. 11, 1992.

*Primary Examiner*—Nashaat T. Nashed
(74) *Attorney, Agent, or Firm*—Browdy and Neimark P.L.L.C.

(57) ABSTRACT

Disclosed are polypeptides which originate from mammal, having L-asparaginase activity. The polypeptides are easily prepared by applying recombinant DNA techniques to DNAs encoding the polypeptides and they exert satisfactory effects in the treatment and/or the prevention for diseases caused by tumor cells dependent on L-asparagine, and cause no substantial serious side effects even when administered to humans in relatively-high dose.

30 Claims, 8 Drawing Sheets

Note: An asterisk indicates a site where a nucleotide is substituted, and a box indicates a polypeptide-encoding sequence.

```
Template DNA         : pCGPA/WT
Sense primer         : 5'-GTGAATTCGGAGGTTCAGATGGCGCGCGCATCA-3'
Anti-sense primer    : 5'-CTGCGGCCGCTCAGATGGCAGGCGGCAC-3'
                     ↓ PCR
              Amplified DNA
                     ↓ Cleavage by Eco RI and Not I
       DNA fragment about 1.7 kbp in length
```

```
              Linkers :

5'-TCGAGCCACCATGAAGTGTTCGTGGGTTATT-3'
              5'-TTCTTCCTGATGGCCGTAGTGACAGGAGTG-3'
              5'-AATTCACTCCTGTCACTACGGCCATCAGGA-3'
              5'-AGAAAATAACCCACGAACACTTCATGGTGGC-3'

↓ Phoshporylation
                          by T4 polynucleotide kinase

5'-terminal phosphorylated linkers
```

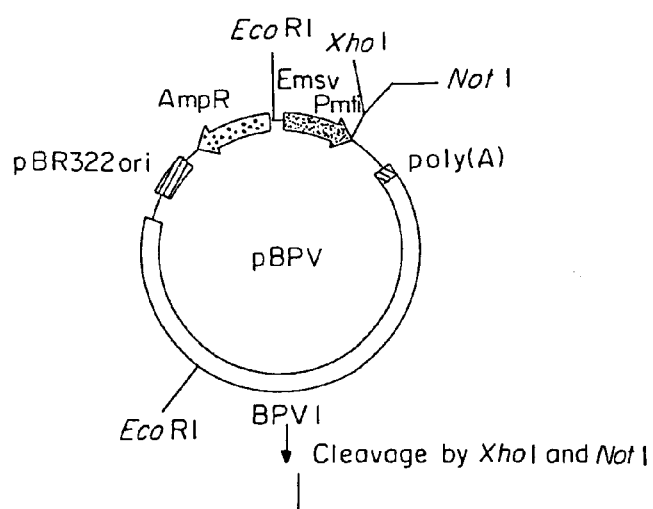

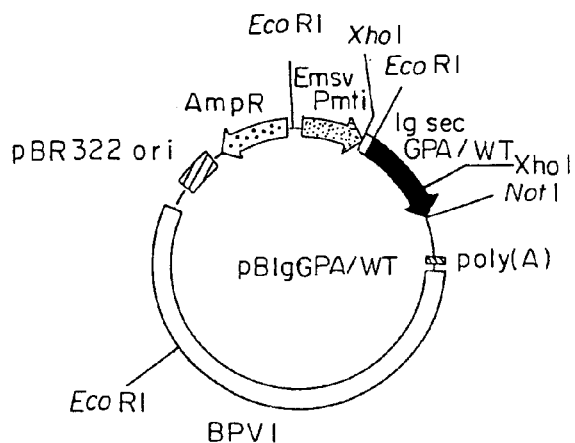

FIG. 3

POLYPEPTIDES HAVING L-ASPARAGINASE ACTIVITY

CROSS-REFERENCE TO RELATED APPLICATIONS

This is a continuation of application Ser. No. 09/195,666, filed Nov. 19, 1998, now U.S. Pat. No. 6,140,101, which is a divisional of application Ser. No. 08/869,927, filed Jun. 5, 1997, the entire contents of both prior applications are incorporated herein entirely by reference.

BACKGROUND OF THE INVENTION

1. Field of the Invention

The present invention relates to L-asparagine amidohydrolytic enzymes, more particularly, to polypeptides which originate from mammal, having L-asparaginase activity.

2. Description of the Prior Art

L-Asparaginase (EC 3.5.1.1) is an enzyme which catalyzes the hydrolytic reaction of L-asparagine into L-aspartic acid and ammonia. The studies on the antitumor activity of L-asparaginase started from the following reports: J. G. Kidd et al. described the inhibitory action of guinea pig sera on cells of lymphomas in "*The Journal of Experimental Medicine*", Vol. 98, pp. 565–582 (1953), and J. D. Broome et al. evidenced in "*Nature*", Vol. 191, pp. 1,114–1,115 (1961), that the L-asparaginase activity of the guinea pig sera was responsible for the inhibitory action. It is now understood that the inhibitory action is caused by the lack of L-asparagine, an essential nutrient to proliferate and survive for some tumor cells which defect L-asparagine synthetase activity, such as acute lymphocytic leukemia, but not for normal cells. The hydrolysis of L-asparagine by L-asparaginase in patients with such tumor cells induces selective death of the tumor cells, resulting in the treatment of malignant tumors.

L-Asparaginase has been studied energetically for its actual use as an antitumor agent, and one derived from *Escherichia coli* is now in use as a therapeutic agent for leukemia and lymphoma. However, L-asparaginase from *Escherichia coli* is merely an external protein for human, and repetitive administration of conventional compositions with such L-asparaginase may cause serious side effects such as anaphylaxis shock, urticaria, edema, wheeze and dyspnea. These compositions are inevitably restricted with respect to administration dose and frequency. Therefore, some proposals to reduce or even diminish such side effects have been given.

As a first proposal, Japanese Patent Kokai No. 119,082/79 discloses a chemically modified L-asparaginase from *Escherichia coli*, in which at least 65% amino acids are blocked with 2-O-substituted polyethylene glycol-4, 6-dichloro-S-triazine. As a second proposal, human L-asparaginases are disclosed in Japanese Patent Kokai Nos. 320,684/92 and 19,018/80, where the L-asparaginases are respectively obtained from cultures of human cell lines and human urine. While the first proposal has an advantage of that the L-asparaginase from *Escherichia coli* is easily obtainable on an industrial scale, it has a disadvantage of that the modifying reaction is difficult to control and the side effects couldn't be eliminated completely. While the second proposal has an advantage of that unlike L-asparaginase from *Escherichia coli*, the L-asparaginases from human may not substantially induce antibodies even when administered to patients, it has a disadvantage of that it is not easy to obtain the L-asparaginases in a desired amount by the processes disclosed in Japanese Patent Kokai Nos. 320,684/92 and 19,018/80.

Recently, recombinant DNA technology has advanced remarkably. If a DNA which encodes a desired polypeptide is once isolated, it is relatively easy to obtain a transformant which produces the polypeptide by constructing a recombinant DNA, comprising the DNA and a self-replicable vector, followed by introducing -the recombinant DNA into a host, such as a microorganism, einimal- or plant-cell. The polypeptide is obtainable in EL desired amount from the culture of the transformant. However, no DNA which encodes mammalian L-asparaginase was isolated, and no mammalian L-asparaginase was produced by recombinant DNA techniques.

Therefore, it has been in great demand to isolate DNAs which encode active L-asparaginases originating from mammal and establish processes to prepare the L-asparaginases on a large-scale by applying the recombinant DNA techniques to the isolated DNAs.

SUMMARY OF THE INVENTION

In view of foregoing, the first object of the present invention is to provide a polypeptide which originates from mamma, having L-asparaginase activity.

The second object of the present invention is to provide a DNA which encodes the polypeptide.

The third object of the present invention is to provide a recombinant DNA which containing a DNA which encodes the polypeptide and a self-replicable vector.

The fourth object of the present invention is to provide a transformant obtainable by introducing a DNA which encodes the polypeptide into a host.

The fifth object of the present invention is to provide a process to prepare the polypeptide by using the transformant.

The sixth object of the present invention is to provide an agent for susceptive diseases, containing the polypeptide as an effective ingredient.

The first object of the present invention is attained by polypeptides which originate from mammal, having L-asparaginase activity.

The second object of the present invention is attained by DNAs which encode the polypeptides.

The third object of the present invention is attained by recombinant DNAs containing DNA which encode the polypeptides and a self-replicable vector.

The fourth object of the present invention is attained by transformants obtainable by introducing the DNAs into appropriate hosts.

The fifth object of the present invention is attained by a process to prepare the polypeptides which comprises culturing the transformants and collecting the produced polypeptides from the resultant cultures.

The sixth object of the present invention is attained by agents for susceptive diseases, containing the polypeptides as effective ingredients.

BRIEF EXPLANATION OF THE ACCOMPANYING DRAWINGS

FIG. 3 is a scheme of the preparation of the present recombinant DNA DBIgGPA/WT the sense and anti-sense primers used in the PCR reaction are designated as SEQ ID NO:37 and SEQ ID NO:38, respectively. The linkers shown in FIG. 3 are SEQ ID NOs:39–42.

FIG. 9 is a restriction map of the present recombinant DNA pKHA/MUT5.

Figure 1:
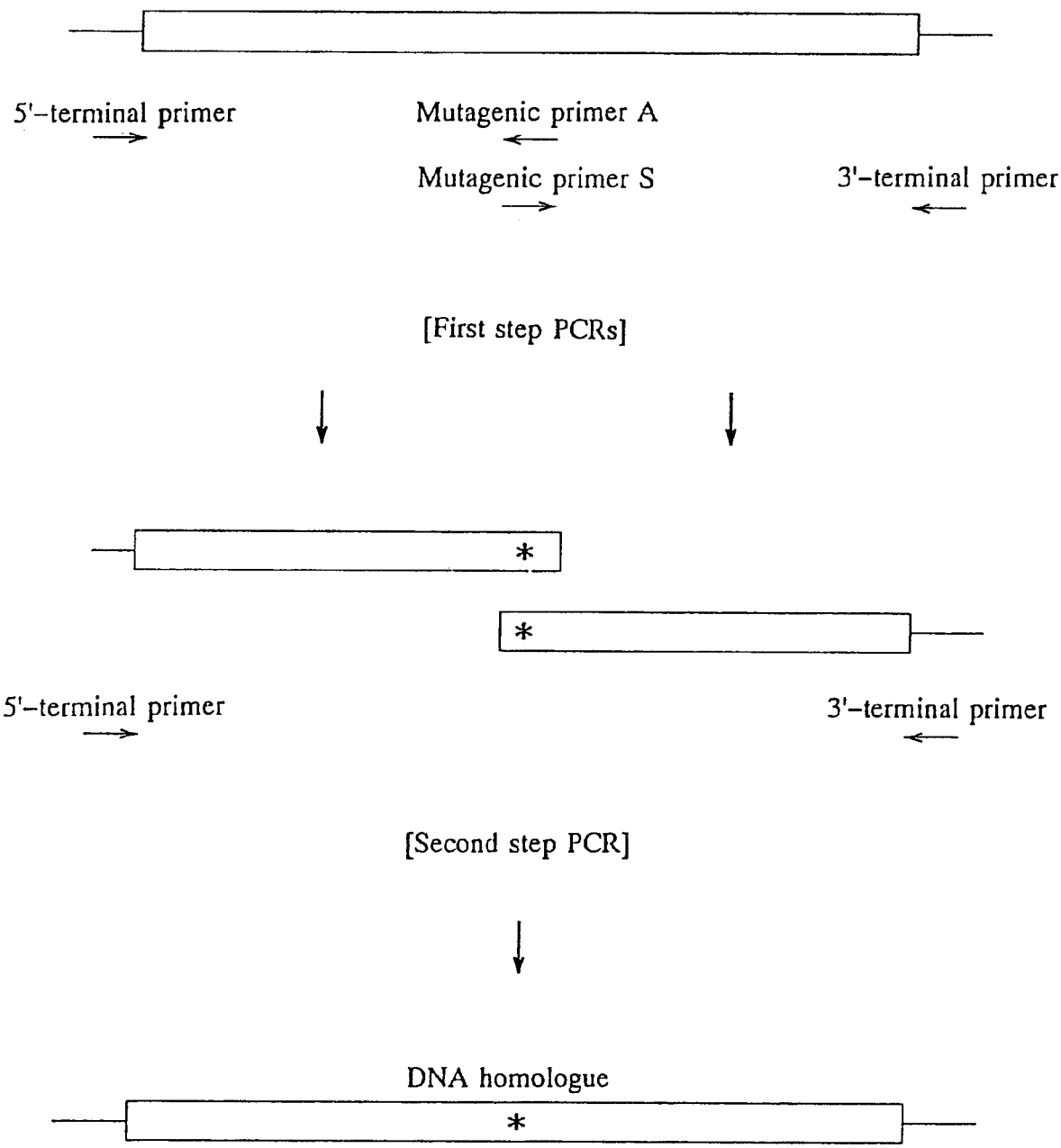
FIG. 1 is a scheme of the over lap extension method.

Explanation of the symbols are as follows:

The symbols, "Eco RI", "Hin dIII", "Not I" and "Xho I", indicate cleavage sites by restriction enzymes, Eco RI, Hin dIII, Not I and Xho I, respectively.

The symbols, "D364stp", "HA/MUT1", "HA/MUT2", "HA/MUT3" and "HA/MUT5",indicate DNAs encoding the present polypeptides.

The symbol "Ptac" indicates a Tac promotor.

The symbol "rrnBTIT2" indicates a region for transcriptional termination, derived from a ribosomal RNA operon.

The symbol "AmpR" indicates an ampicillin resistant gene.

The symbol "pBR322ori" indicates a replication origin in *Escherichia coli.*

The symbol "Ig sec" indicates a DNA encoding a polypeptide with a signal sequence for secretion of immunoglobulin.

The symbol "Emsv" indicates an enhancer from long terminal repeats of Moloney Mouse Sarcoma Virus.

The symbol "Pmti" indicates a promotor for Mouse metallothionein I gene.

The symbol "Poly (A)" indicates a polyadenylation signal derived from SV40 virus.

The symbol "BPVI" indicates a genome of a bovine paplliomavirus.

DETAILED DESCRIPTION OF THE INVENTION

The present inventors isolated mammalian DNAs encoding L-asparaginases firstly in the world, from guinea pig and human, and succeeded in elucidating their nucleotide sequences. The nucleotide sequences of the DNAs from a guinea pig and human are in SEQ ID NOs:15 and 16, respectively. This information is disclosed in Japanese Patent Application No. 42,564/95 (Japanese Patent Kokai No. 214,885/96) by the same applicant of this application. The present invention has been made based on the above information, and provides the polypeptides which originate from mammal, having L-asparaginase activity.

The polypeptides of the present invention are not restricted to their sources or origins so far as they originate from mammal and have an L-asparaginase activity. The polypeptides are usually obtainable by the expression of genes originating from mammal, and usually contain amino acid sequences of SEQ ID NOs:1 to 3, wherein the symbol "Xaa" in SEQ ID NO:3 means "glutamine" or "arginine". For example, the polypeptides have any one of amino acid sequences of SEQ ID NOs:4 to 9. In view of the technical level in this field, one or more amino acid residues in SEQ ID NOs:4 to 9 can be substituted relatively easily by different ones without substantial defects of the activity. Despite derived from the same DNA, a variety of polypeptides with an L-asparaginase activity may be obtained as a result of modifications by endogenous enzymes of the hosts after the DNA expression or modifications during purification of the polypeptides, depending on the types of vectors and hosts used to obtain transformants or culturing conditions of the transformants, such as ingredients, compositions, temperatures or pHs. The wording "a variety of polypeptides" includes the polypeptides with deletions and/or additions of one or more amino acids at the N-and/or C-termini thereof, or with glycosylations. In view of these, the present polypeptides include not only the polypeptide with any amino acid sequence of SEQ ID NOs:4 to 9 but also their homologues so long as they have an L-asparaginase activity. The present polypeptides express the activity when exist in multiple forms, preferably, tetramers.

The polypeptides of the present invention can be usually prepared by the recombinant DNA techniques. In general, the polypeptides are obtainable by culturing transformants containing DNAs encoding the polypeptides and collecting the produced polypeptides from the resultant cultures. The transformants are obtainable by introducing such recombinant DNAs as contain any one of the nucleotide sequences of SEQ ID Nos:10 to 15 and a self-replicable vector into appropriate hosts. One or more nucleotides in SEQ ID NOs:10 to 15 can be substituted by different nucleotides without substantial changes of the encoding amino acid sequences with respect to degeneracy of genetic code. To facilitate the expression of the DNA in the hosts, one or more nucleotides in nucleotide sequences which encode the polypeptides or their homologues can be appropriately substituted by different ones. Furthermore, nucleotide sequences which encode and/or don't encode one or more amino acids can be added to the 5'- and/or 3'-termini of the nucleotide sequences.

The DNAs encoding the polypeptides of this invention include those from natural sources and those by synthesized artificially so far as the polypeptides expressed by them have an L-asparaginase activity. The DNAs can be wild-type ones, containing the same nucleotide sequences as those from natural sources, and can be their homologues.

Examples of the wild-type DNAs include DNAs containing the nucleotide sequences of SEQ ID NO:15. The wild-type DNA is obtainable from natural sources such as guinea pig livers, as disclosed in Japanese Patent Application No. 42,564/95 (Japanese Patent Kokai No. 214,885/96) by the same applicant of this invention: (a) constructing a cDNA library by applying usual methods to purified poly (A)$^+$ RNAs from a guinea pig or human liver as materials, (b) applying the plaque hybridization method to the CDNA library using oligonucleotides as probes synthesized chemically based on partial amino acid sequences of L-asparaginase purified from a guinea pig serum, (c) collecting phage clones containing the DNAs encoding the polypeptides of this invention, and (d) manipulating the collected phage clones in a conventional manner. The wild-type DNA can be synthesized chemically based on SEQ ID NO:15.

Examples of DNA homologues to the wild-type ones include DNAs containing any nucleotide sequence of SEQ ID NOs:10 to 14. DNA homologues containing the nucleotide sequence of SEQ ID NO:10 are obtainable by applying conventional methods in this field, such as PCR method and methods for site-directed mutagenesis, to the wild-type DNA of SEQ ID NO:15 concerning the desired sequence. DNA homologues containing any nucleotide sequence of SEQ ID NOs:11 to 14 are obtainable by the methods such as follows: Firstly, A wild-type DNA with the nucleotide sequence of SEQ ID NO:16 is obtained by the methods as disclosed in Japanese Patent Application No. 42,564/95 (Japanese Patent Kokai No. 214,885/96) by the same applicant of this invention, i.e., screening a human liver cDNA library. Subsequently, the wild-type DNA is subjected to conventional methods as mentioned above concerning desired sequences to obtain the DNA homologues. The DNA homologues can be synthesized chemically based on the nucleotide sequences of SEQ ID NOs:10 to 14.

The present DNAs can be generally introduced into hosts as in forms of recombinant DNAs. In general, each recombinant DNA comprises one of the present DNAs and a self-replicable vector. The recombinant DNAs can be easily prepared by general recombinant DNA techniques when the DNAs are available. Examples of such self-replicable vectors include pKK223-3, pGEX-2T, pRL-λ, pBTrp2 DNA, pUB110, YEpl3, Ti plasmid, Ri plasmid, pBI121, pCDM8, pBPV and BCMGSneo. Among these vectors, pKK223-3, pGEX-2T, pRL-λ, pBTrp2 DNA pUB110 are suitably used to express the present DNAs in prokaryotic cells such as *Escherichia coli* and Bacillus sp., while YEpl3, Ti plasmid, Ri plasmid, pBI121, pCDM8, PBPV and BCMGSneo are suitably used to express the present DNAs in eukaryotic cells such as yeasts and animal- and plant-cells.

To insert the present DNAs into the vectors, conventional methods in this field can be arbitrarily used. Examples of such methods contain the steps of (a) cleaving self-replicable vectors with restriction enzymes, (b) introducing the same cleavage sites, by the same restriction enzymes as used to cleave the vectors, to the 5'- and 3'-termini of the present DNAs by applying polymerase chain reaction to form double-stranded DNAs, (c) cleaving the double-stranded DNAs by the restriction enzymes, and (d) ligating the cleaved vectors with cleaved DNAs by the action of DNA ligases. The recombinant DNAs thus obtained can be easily introduced into appropriate hosts, resulting in limitless replication of the DNAs by culturing the transformants.

The recombinant DNAs according to the present invention can be introduced into appropriate hosts such as *Escherichia coil*, Bacillus sp., actinomycetes, yeasts and plant-and animal-cells. To introduce the DNAs into *Escherichia coli*, it can be cultured in the presence of the recombinant DNAs and calcium ion. To introduce them into Bacillus sp., competent cell methods or protoplast methods can be used. To introduce them into animal-cells, DEAE-dextran methods or electroporation methods can be used. Desired transformants can be cloned by applying hybridization methods or by selecting L-asparaginase producing cells from the cultures.

The transformants thus obtained produce the present polypeptides intracellularly or extracellularly when cultured in nutrient culture media. Examples of such media are usually liquid nutrient culture media which generally contain carbon sources, nitrogen sources and minerals, and further contain micronutrients such as amino acids and/or vitamins on demand. The carbon sources usable in the present invention include saccharides such as starch, starch hydrolysates, glucose, fructose and sucrose. The nitrogen sources usable in the present invention include organic and inorganic compounds containing nitrogen, such as ammonia and their salts, urea, nitrates, peptone, yeast extract, defatted soy bean, corn steep liquor and beef extract. Cultures containing the present polypeptides can be obtained by inoculating the transformants into the above media, culturing them at temperatures of 25–65° C. at pHs of 5–8 for about 1–10 days under aerobic conditions by aeration-agitation method, etc.

The cultures can be used intact as agents for susceptive diseases. However, the cultures are usually treated with ultrasonication or cell wall lytic enzymes to disrupt cells, and the present polypeptides are separated by using techniques such as filtration and centrifugation from the cell-disruptants and purified. Alternatively, the polypeptides can be purified from the culture supernatants obtained by removing cells from the cultures by filtration or centrifugation, etc. The present polypeptides can be purified by applying techniques generally used in this field for protein purifications, such as salting out, dialysis, filtration, concentration, gel filtration chromatography, ion-exchange chromatography, affinity chromatography, hydrophobic chromatography, iso-electric focusing and gel electrophoresis, and if necessary, two or more of them can be applied combination to the supernatants which are separated from insoluble substances of cell-disruptants, or to the culture supernatants. The resultant purified solutions polypeptides can be concentrated and/or lyophilized into liquids or solids depending on their final uses.

The following experiments explain the present invention in more detail, and the techniques used therein are conventional ones in this field: For example, the techniques are disclosed by J. Sambrook et al. in *"Molecular Cloning, A Laboratory Manual"*,2nd edition (1989), published by Cold Spring Harbor Laboratory Press, New York, U.S.A., and by Masami MATSUMURA in *"Laboratory Manual for Genetic Engineering"* (1988), published by Maruzen Co., Ltd., Tokyo, Japan.

EXPERIMENT 1

Expression of Wild-type DNA

EXPERIMENT 1-1

Expression of Guinea Pig Wild-type DNA

EXPERIMENT 1-1(a)

Preparation of Guinea Pig Wild-type DNA

A guinea pig wild-type DNA encoding L-asparaginase was prepared by the method disclosed in Japanese Patent Kokai No. 214,885/96 by the same applicant of this invention. The DNA had the nucleotide sequence of SEQ ID NO:15. A DNA having a polypeptide-encoding region in SEQ ID NO:15, i.e., a sequence of containing the nucleotides 20-1,714 in SEQ ID NO:15, is called "GPA/WT DNA" hereinafter, and the expression product thereof with the amino acid sequence of SEQ ID NO:49 is called "guinea pig wild-type L-asparaginase".SEQ ID NO:17 shows in parallel the nucleotide sequence of GPA/WT DNA and the amino acid sequence SEQ ID NO:49 encoded thereby.

EXPERIMENT 1-1(b)

Preparation of Recombinant DNA

Ten μl of 10×PCR buffer, one μl of 25 mM dNTP mix, one ng of the human wild-type DNA, obtained in Experiment 1-1(a), as a template were placed in 0.5 ml reaction tube. The mixture was mixed with, as a sense- and anti-sense-primers, an adequate amount of an oligonucleotide chemically synthesized based on the amino acid sequences near the N- and C-termini of SEQ ID NO:15, volumed up with sterilized distilled water to give a total volume of 99.5 μl, and mixed with 0.5 μl of 2.5 units/μl of AmpliTaq DNA polymerase. The nucleotide sequence of the sense primer was 5'-AATCTCGAGCCACCATGGCGCGCGCATCA-3'SEQ ID NO:19, a nucleotide sequence obtained by adding a common nucleotide sequence in animal cells, as shown by M. Kozak in "Nucleic Acid Research", Vol. 15, pp. 8,125–8, 148 (1987), to the upstream of a region which encodes the N-terminal amino acid sequence of SEQ ID NO:15 and then adding to the further upstream a cleavage site by a restriction enzyme, Xho I. The nucleotide sequence of the anti-sense primer was 5'-CTGCGGCCGCTTATCAGATGGCAGGCGGCAC-3'SEQ ID NO:20 as a complement to a nucleotide sequence obtained by adding two termination codons to the downstream of a region which encodes the C-terminus of the amino acid sequence of SEQ ID NO:15 and adding a cleavage site by a restriction enzyme, Not I, to the further downstream. The resulting mixture was successively incubated at 94° C. for one min, at 55° C. for one min, and at 72° C. for 3 min, and the series of incubation was repeated 40-times for PCR to amplify DNA. Thus, a DNA containing GPA/WT DNA was obtained and then cleaved by restriction enzymes of Xho I and Not I to obtain an about 1.7 kbp DNA fragment. Twenty-five ng of the DNA fragment was weighed and mixed with 10 ng of a plasmid vector, "pCDM8", commercialized by Invitrogen Corporation, San Diego, U.S.A., which had been cleaved by restriction enzymes of Xho I and Not I. To the DNA mixture thus obtained was added an equal volume of the solution I in, "LIGATION KIT VERSION 2" commercialized by Takara Shuzo, Tokyo, Japan, and incubated at 160° C. for 2 hours to obtain a replicable recombinant DNA, "pCqGPA/WT".

The recombinant DNA pCGPA/WT was introduced into an *Escherichia coil* MC1061/P3 strain, commercialized by Invitrogen Corporation, San Diego, U.S.A., by competent cell method. The transformant thus obtained was inoculated into L broth medium (pH 7.2) containing 20 μg/ml ampicillin and 10 μg/ml tetracycline followed by cultivation at 37° C. for 18 hours under shaking conditions. The transformants were collected from the culture by centrifugation and subjected to conventional alkali-SDS method to extract the recombinant DNA pCGPA/WT. The analysis of the pCGPA/WT by an automatic sequencer equipped with a fluorophotometer confirmed that it contained GPA/WT DNA, which termination codons were ligated to the 3'-terminus and was ligated to the downstream of a CMV promotor from the 5'- to 3'-termini.

The system using COS-1 (ATCC CRL-1650) as a host, which is a cell line derived from a monkey kidney, was used to express the DNA in the following Experiments 1 and 2. Since the system is for a transient expression, it has a disadvantage that DNAs introduced into transformants could not be stable over several days, and the transformants do not produce the desired polypeptides repeatedly. However, it is known that the number of copies of the desired DNA per cell temporally increases to $10^5$ when plasmid vectors having a replication origin derived from SV40 virus, such as the above mentioned pCDM8, are introduced into the COS-1 cells. With this point of view, the system has a merit that it quite easily analyzes the desired DNA-expression product.

EXPERIMENT 1-1(c)

Recombinant DNA Expression in COS-1 Cell

In accordance with the DEAE-dextran method reported by Frederick M. Ausubel et al. in "*Current Protocols in Molecular Biology*" (1987), chapters 9.2.1–9.2.3 and 9.2.5–9.2.6, published by John Wiley and Sons Inc., New York, U.S.A., the recombinant DNA pCGPA/WT in Experiment 1-1(b) was introduced into COS-1 cells for its expression. To each well of "3046", a plastic multiwall plate, with 6 wells of 3.5 cm diameter, commercialized by Becton Dickinson Labware, New Jersey, U.S.A., was added 2.5 ml of DME medium, containing 10 v/v % bovine fetal serum and $1.8 \times 10^5$ COS-1 cells. The cells were cultured at 37° C. in a 5 v/v % $CO_2$ incubator overnight. After removing the culture supernatant by an aspirator and washing the remaining cells with DME medium containing 50 mM Tris-HCl buffer (pH 7.4), each well was charged with 2.5 ml of DME medium containing 2.8 μg/ml PCGPA/WT, 50 Mm Tris-HCl (pH 7.4), 0.4 mg/ml DEAE-dextran and 0.1 mM chloroquine, and incubated at 37° C. for 4 hours in a 5 v/v % $CO_2$ incubator. Thereafter, the culture supernatant was removed, and the remaining cells in each well were received with 2.5 ml of 10 mM phosphate buffered saline (hereinafter abbreviated as "PBS") containing 10 v/v % DMSO before incubating at ambient temperature for 2 minutes. After removing the supernatant and washing the remaining cells with DME medium containing 50 mM Tris-HCl (pH 7.4), each well was charged with 2.5 ml of "COS MEDIUM", commercialized by COSMO BIO CO. LTD., Tokyo, Japan, followed by cultivation at 37° C. for 3 days in a 5 v/v % $CO_2$ incubator to express the desired DNA. As a control, the same experiment was carried out using a plasmid vector, pCDM8.

After 3 days' cultivation, the multiwell plates with the cultures were subjected thrice to a treatment of freezing at −80° C. and thawing at ambient temperature to disrupt the cells. The whole cultures were transferred to centrifugal tubes and centrifuged to remove insoluble components after precipitated, followed by obtaining total soluble fractions, concentrating the fractions using membranes, and adjusting the volume of the total soluble fraction per well to give 0.5 ml for the following analyses.

EXPERIMENT 1-1(d)

Assay for L-asparaqinase Activity

L-Asparaginase activity was expressed by the unit assayed as follows: Samples were placed in 1.5 ml-reaction tubes in 50 μl each and admixed with 200 μl of 50 mM phosphate buffer (pH 7.0) containing 1.4 mg/ml L-asparagine. After standing at 37° C. for 0, 1, 2, 4, 6 and 16 hours, L-aspartic acid in the reaction mixtures was quantified by an amino acid analyzer. In parallel, 1.0, 0.5 and 0.25 unit/ml dilutions of an L-asparaginase from *Escherichia coli* were provided and quantified for L-aspartic acid after incubating at 37° C. for 0 and one hour, and based on the increased amount of L-aspartic acid, a calibration curve was drawn. By plotting on the calibration curve the increased amounts of L-aspartic acid of the samples, the samples' L-asparaginase activities were estimated. The activity of samples with a lower activity was estimated based on that assayed after 2 hours or more incubation. One unit activity of L-asparaginase was defined as the amount that releases one µmol of ammonia from L-asparagine per minute under the above conditions.

The total soluble fractions obtained in Experiment 1-1(c) were treated similarly as above, and expressed their activities as total L-asparaginase activities that were detected in the soluble fractions from 1.8×105 COS-1 cells. As a result, the activity of the total soluble fraction in Experiment 1-1(c) was 0.083 unit, and the control gave no activity.

EXPERIMENT 1-1(e)

Western Blotting

An anti-L-asparaginase antibody was prepared as follows: An oligopeptide of a sequence Gly-Ser-Gly-Asn-Gly-Pro-Thr-Lys-Pro-Asp-Leu-Leu-Gln-Glu-Leu-Arg-Cys-(SEQ ID NO:21) was synthesized chemically in a usual manner. Keyhole Limped Hemocyanin was linked to the C-terminus of the oligopeptide. The resultant was purified and used to immunize rabbits in a usual manner. The rabbits were immunized 6 times 2 weeks about, then the whole blood was collected and subjected to salting out with 50 w/v % ammonium sulfate to obtain an anti-L-asparaginase antiserum.

In accordance with the method reported by U. K. Laemli et al. in "*Nature*",Vol. 227, pp. 680–685 (1970), 0.2 ml of the total soluble fraction in Experiment 1-1(c) was subjected to 12.5 w/v % SDS-poiyacrylamide gel electrophoresis (hereinafter abbreviated as "SDS-PAGE"). The polypeptides migrated were transferred to a nitrocellulose membrane and subjected to Western blotting using the above anti-L-asparaginase anti-serum, in accordance with the method reported by H. Towbin in "*Proceedings of the National Academy of Sciences of the U.S.A.*", Vol. 76, pp. 4,350–4,354 (1979). For color development, alkaline phosphatase system was used. Comparing with the control and molecular weight markers, both the identification of bands specifically stained in the sample and the measurement of the molecular weight of each subunit of the L-asparaginase were carried out. The molecular weight markers used were bovine serum albumin (67 kDa), ovalbumin (45 Kda), soy bean trypsin inhibitor (20.1 kDa) and α-lactalbumin (14.4 kDa), and stained with amide black. The total soluble fraction in Experiment 1-1(c) gave no clear band.

EXPERIMENT 1-1(f)

Measurement of Molecular Weight on Gel Filtration

Two ml of the total soluble fraction in Experiment 1-1(c) was subjected to gel filtration column chromatography using "HILOAD SUPERDEX 200 COLUMN",with an inner diameter of 16 mm and a length of 60 cm, commercialized by Pharmacia LKB Biotechnology AB, Uppsala, Sweden, equilibrated with PBS. Based on the L-asparaginase activity of the eluted fractions, the molecular weight of the guinea pig wild-type L-asparaginase in a native form was examined. The molecular weight markers used were thyroglobulin (699 kDa), ferritin (440 kDa), catalase (232 kDa), aldolase (158 kDa), bovine serum albumin (67 kDa) and ovalbumin (43 kDa). The peak of L-asparaginase activity in the eluted fractions was observed in a position corresponding to a molecular weight of about 300 kDa.

Since no clear band was detected by Western blotting, the molecular weight of the wild-type L-asparaginase in a dissociated form could not be detected, while the molecular weight in a native form was estimated to be about 300 kDa based on the result of gel filtration. The molecular weights of L-asparaginase in a native and dissociated form, purified from guinea pig L-asparaginase in serum, were respectively estimated to be about 190 kDa on gel filtration and about 43 kDa on DS-PAGE. As disclosed in Japanese Patent Kokai No. 214,885/96 by the same applicant of the present invention, 3 partial amino acid sequences of a guinea pig L-asparaginase in serum were observed in a region of amino acids 10–236 in the sequence of guinea pig wild-type L-asparaginase. While, two consensus amino acid sequences essential for the expression of L-asparaginase activity, i.e., SEQ ID NOs:1 and 2, as proposed by E. Harms in "FEBS letters",Vol. 285, pp. 55–58 (1991) based on the results of experiments on L-asparaginase derived from *Escherichia coli*, correspond to the sequences of amino acids 16–19 and 114–118 in the amino acid sequence of the guinea pig wild-type L-asparaginase. In view of these and the results in Experiment 1-1, the present inventors estimated that the guinea pig wild-type L-asparaginase may require a region of amino acids about 1–400 in the amino acid sequence to express the activity. In Experiment 2-1, to examine the L-asparaginase activities of C-terminal defective mutants as homologues of the guinea pig wild-type L-asparaginase, the expression products of DNA homologues from a guinea pig were tested for properties and features.

EXPERIMENT 1-2

Expression of Human Wild-type DNA

A human wild-type DNA encoding L-asparaginase was prepared according to the method in Japanese Patent Kokai No. 214,855/96 by the same applicant of the present invention. The DNA had the nucleotide sequence of SEQ ID NO:16. Hereinafter, a DNA having a polypeptide-encoding region in SEQ ID NO:16, i.e., a sequence of nucleotides 93–1,811 in SEQ ID NO:16, was named "HA/WT DNA", and a polypeptide, as the expression product of HA/WT DNA, having the amino acid sequence of SEQ ID NO:50, may be called "human wild-type L-asparaginase". SEQ ID NO:18 shows the nucleotide sequence of GPA/WT DNA and the amino acid sequence SEQ ID NO:50 encoded thereby.

Except for the template and the sense- and anti-sense-primers, PCR was performed under the same conditions as used in Experiment 1-1(b). As a template, the human wild-type DNA in Experiment 1-2 was used. As a sense- and anti-sense-primers, oligonucleotides with sequences of 5'-AATCTCGAGCCACCATGGCGCGCGCG GTG-3'SEQ ID NO:22 and 5'-CTGCGGCCGCTTATCAGACACCAGGCAGCAC-3'SEQ ID NO:23 were respectively uses. The DNA thus amplified was continuously treated with the same method as used in Experiment 1-1(b) to prepare a recombinant DNA, "pCHA/WT".After sequencing, the pCHA/WT was introduced into COS-1 cells and expressed followed by analyzing the expression product similarly as in Experiment 1-1.

In contrast to the guinea pig wild-type L-asparaginase, the experiment system could not detect the human wild-type L-asparaginase activity. It was presumably due to that the human wild-type L-asparaginase had a lower specific activity than that of the guinea pig wild-type one, and this forced to examine the properties of expression products by DNA homologues from human in Experiment 2-2.

EXPERIMENT 2

Expression of DNA Homoloque

EXPERIMENT 2-1

Expression of DNA Homoloque Originating From Guinea Pig

A termination codon was replaced for the nucleotide sequence in a specific position of the guinea pig wild-type DNA to obtain a DNA homologue: A DNA was obtained by PCR method by replacing a termination codon for a codon of the nucleotides 1,090–1,092 or 1,012–1,014 in SEQ ID NO:17. Except for the nucleotide sequence of anti-sense primer, PCR was performed under the same conditions as used in Experiment 1-1(b). As an anti-sense primer, an oligonucleotide with a sequence of 5'-CTGCGGCCGCTTATCATGCCGTGGGCAGTGT-3'SEQ ID NO:24 or 5'-CTGCGGCCGCTTATCACCCAACACGTAGGA-3'SEQ ID NO:25 was used to prepare the two-types of DNAs. The amplified DNAs were treated similarly as in Experiment 1-1(b) to obtain recombinant DNAs, "pCGPA/D364stp" and "pCGPA/L338stp". By sequencing similarly, it was confirmed that pCGPA/D364stp and pCGPA/L338stp had DNAs, encoding the sequences of amino acids 1-363 and 1-337 in the guinea pig wild-type L-asparaginase, respectively, and had a termination codon at their 3'-termini free of intervening sequences. Hereinafter, the polypeptide-encoding regions of the DNAs are respectively named "GPA/D364stp DNA" and "GPA/L338stp DNA". GPA/D364stp DNA and GPA/L338stp DNA were ligated in the downstream of a CMV promoter in the direction from the 5'- to 3'-termini. The DNAs expression products may be named "guinea pig t-asparaginase homologues".

The above recombinant DNAs were introduced into COS-1 cells and examined similarly as in Experiment 1-1. As controls, pCGPA/WT and pCDM8 in Experiment 1-1(b) were similarly treated and examined. Table 1 shows the results.

TABLE 1

| Recombinant DNA | L-asparaginase activity (unit) | Molecular weight (kDa) *1 | Molecular weight (kDa) *2 |
|---|---|---|---|
| pCGPA/WT | 0.083 | — | about 300 |
| pCGPA/D364stp | 0.228 | about 40 | about 140 |
| pCGPA/L338stp | N.D. *3 | about 40 | — |
| pCDM8 | N.D. *3 | — | — |

Note: The symbols "*1", "*2" and "*3" mean that the value was determined by Western blotting, the value was determined by gel filtration, and the activity was not detected, respectively.

As shown in Table 1, the activities of the expression products of GPA/PWT DNA and GPA/D364stp DNA were detected, but not for GPA/L338stp DNA. These results suggest that a region of amino acids 1–363 in the guinea pig wild-type L-asparaginase may be enough for sufficiently expressing the L-asparaginase activity. This amino acid sequence, amino acids 1–363 in the guinea pig wild-type, is SEQ ID NO:4, and a nucleotide sequence which encodes the amino acid sequence is SEQ ID NO:10. The amino acid sequence of the guinea pig wild-type L-asparaginase is SEQ ID NO:5.

EXPERIMENT 2-2

Expression of DNA Homoloque Originating From Human

DNA homologues were prepared by replacing specific codons in the human wild-type DNA with termination codons or codons for different amino acids: The DNA homologues were prepared by replacing termination codons for the nucleotides 1096–1098 in SEQ ID NO:18 by applying PCR method. Except for the template and the sense- and anti-sense-primers, PCR was performed under the same conditions as used in Experiment 1-1(b). As a template, the human wild-type DNA in Experiment 1-2 was used. As a sense- and anti-sense-primers, the oligonucleotides with sequences of 5'-AATCTCGAGCCACCATGGCGCGCGCGGTG-3'SEQ ID NO:22 and 5'-CTGCGGCCGCTCATTACACCGAGGGTGGCGT-3'SEQ ID NO:26 were respectively used. The amplified DNA was treated similarly as in Experiment 1-1 to obtain a recombinant DNA, "pCHA/E366stp", and sequenced. It was confirmed that pCHA/E366stp contained a DNA encoding amino acids 1–365 in SEQ ID NO:50 and a termination codon at the 3'-terminus free of intervening sequences. The polypeptide-encoding region was named "HA/El366stp DNA", hereinafter. HA/E366stp DNA was ligated to the downstream of a CMV promotor in the direction from the 5'- to 3'-termini.

To change specific codons in DNAs into ones for different amino acids, the over lap extension method reported by Robert M. Horton et al. in "Methods in Enzymology", Vol. 217, pp. 270–279 (1993), published by Academic Press, Inc., San Diego, U.S.A., was used. The method is summarized in FIG. 1 and explained as follows: First, mutagenic primers A and B, where the nucleotides to be mutagenized were substituted by desired different ones complementary to one another, were prepared. The mutagenic primer A was a sense strand, and the mutagenic primer B was an anti-sense strand. A set of 5'- and 3'-terminal primers, which amplify the whole region of the desired DNA, were a prepared, and they were respectively a sense- and anti-sense-strands. Second, conventional PCR was performed using the 5'-terminal primer, the mutagenic primer A, and as a template, a DNA with the original nucleotide sequence. In parallel, another PCR as was performed using the same DNA as a template, the 3'-terminal primer, and the mutagenic primer B. These two PCRs were named "first step PCRs". Third, two DNAs amplified in the first step PCRs were mixed with the 5'- and 3'-terminal primers as used in the first step PCRs followed by performing PCR as a second step PCR. The two DNA fragments amplified in the first step PCRs were used as primers and templates to generate mutagenized DNAs, while the 5'- and 3'-terminal primers were used as primers to amplify the mutagenized DNAs. By this method, DNAs into which were introduced 7 types nucleotide substituents, i.e., 7 DNA homologues were prepared. The 7 types nucleotide substituents and consequent changes of the encoded amino acid sequences are summarized in Table 2. The template DNA and mutagenic primers A and B used to prepare the 7 DNA homologues were summarized in Table 3. The 5'- and 3'-terminal primers were respectively equal to the sense- and anti-sense-primers as used to prepare pCHA/E366stp in Experiment 2-2.

TABLE 2

| DNA homologue | Recombinant DNA | Nucleotide substitution (upper line) and consequential change of amino acid (lower line)* |
|---|---|---|
| HA/MUT1 DNA | pCHA/MUT1 | C894G, A902G, G952A, G953A and G1096T |
| | | H298Q, Q301R, G318N and E366stp |
| HA/MUT2 DNA | pCHA/MUT2 | C894G, A902G and G1096T |
| | | H298Q, Q301R and E366stp |
| HA/MUT3 DNA | pCHA/MUT3 | C894G, G952A, G953A and G1096T |
| | | H298Q, G318N and E366stp |
| HA/MUT4 DNA | pCHA/MUT4 | A902G, G952A, G953A and G1096T |
| | | Q301R, G318N and E366stp |
| HA/MUT5 DNA | pCHA/MUT5 | C894G and G1096T |
| | | H298Q and E366stp |
| HA/MUT6 DNA | pCHA/MUT6 | A902G and G1096T |
| | | Q301R and E366stp |
| HA/MUT7 DNA | pCHA/MUT7 | G952A, G953A and G1096T |
| | | G318N and E366stp |

*Numbers in the upper lines in each column mean a nucleotide number in SEQ ID NO:18. Numbers in the lower lines in each column means an amino acid residue number in SEQ ID NO:18. Alphabets on the left and right of the numbers in the upper lines show nucleotides before and after the nucleotide substitution, respectively. Alphabets on the left and right of the numbers in the lower lines show amino acids before and after the nucleotide substitution, respectively. The symbol "stp" means that a termination condon was substituted for a codon in the wild-type DNA. Names for the 7 DNA homologues and the recombinant DNAs containing the DNA homologues are shown in parallel.

TABLE 3

| DNA homologue | Template DNA | Nucleotide sequences of mutagenic primers A (upper line) and B (lower line) * |
|---|---|---|
| HA/MUT1 DNA | pCHA/MUT7 | the same as used for HA/MUT2 DNA preparation |
| | | the same as used for HA/MUT2 DNA preparation |
| HA/MUT2 DNA | pCHA/E366stp | 5'-CCCCcGGAGGCAcTGGGT-3'(SEQ ID NO:27) |
| | | 5'-ACCCAgTGCCTCCgGGGG-3'(SEQ ID NO:28) |
| HA/MUT3 DNA | pCHA/MUT7 | the same as used for HA/MUT5 DNA preparation |
| | | the same as used for HA/MUT5 DNA preparation |
| HA/MUT4 DNA | pCHA/MUT7 | the same as used for HA/MUT6 DNA preparation |
| | | the same as used for HA/MUT6 DNA preparation |
| HA/MUT5 DNA | pCHA/E366stp | 5'-CCCCTGGAGGCAcTGGGT-3'(SEQ ID NO:29) |
| | | 5'-ACCCAgTGCCTCCAGGGG-3'(SEQ ID NO:30) |
| HA/MUT6 DNA | pCHA/E366stp | 5'-CCCCcGGAGGCAGTGGGT-3'(SEQ ID NO:31) |
| | | 5'-ACCCACTGCCTCCgGGGG-3'(SEQ ID NO:32) |
| HA/MUT7 DNA | pCHA/E366stp | 5'-GACGttGGCTCCCGCCAT-3'(SEQ ID NO:33) |
| | | 5'-ATGGCGGGAGCCaaCGTC-3'(SEQ ID NO:34) |

Note:
Small letters mean nucleotides which were substituted for those in human wild-type DNA.

compare quantitatively the expressed products. The results were in Table 4.

TABLE 4

| Recombinant DNA | L-asparaginase activity (unit) *1 | Molecular weight (kDa) *2 | Quantity *3 | Molecular weight (kDa) *4 |
|---|---|---|---|---|
| pCHA/WT | N.D. | — | — | — |
| pCHA/E366stp | N.D. | about 40 | 2.3 | — |
| pCHA/MUT1 | 0.021 | about 40 | 0.4 | about 140 |
| pCHA/MUT2 | 0.031 | about 40 | 0.9 | about 140 |
| pCHA/MUT3 | 0.009 | about 40 | 0.1 | about 140 |
| pCHA/MUT4 | N.D. | about 40 | 0.2 | — |
| pCHA/MUT5 | 0.006 | about 40 | 1.2 | about 140 |
| pCHA/MUT6 | N.D. | about 40 | 1.9 | — |
| pCHA/MUT7 | N.D. | about 40 | 0.2 | — |
| pCDM8 | N.D. | — | — | — |

Note: The symbols "*1", "*2", "*3" and "*4" mean the activity was not detected, the value was determined by Western blotting, the value indicates the signal intensity of the band detected on Western blotting and quantified by densitometry, and the value was determined by gel filtration, respectively.

The results in Table 4 indicate that human L-asparaginases both in the wild-type and in the C-terminal defected mutant, i.e., the expression product of HA/E366stp DNA, as the one of the homologues, had a lower specific activity than that from guinea pigs. In addition, these results indicate that the specific activity of L-asparaginases among those of point mutants, which some of the amino acids inherent to the human wild-type L-asparaginase were sub- The obtained DNA homologues from human were treated similarly as in Experiment 1-1 to obtain recombinant DNAs "pCHA/MUT1", "pCHA/MUT2", "pCHA/MUT3", "pCHA/MUT4", "pCHA/MUT5", "pCHA/MUT6" and "?PCHA/MUT7". The expression products of the DNA homologues, obtained in Experiment 2-2, may be named "human L-asparaginase homologues", hereinafter. After sequencing, these DNA homologues were introduced into COS-1 cells, followed by expression and assay. As controls, pCHA/WT obtained in Experiment 1-2 and pCDM8 were treated and examined. Signal intensities of bands, detected by Western blotting, were evaluated by densitometry to stituted by different ones, increased to a detectable level. The human DNA homologues such as HA/MUT1, HA/MIJT2, HA/MUT3 and HA/MUT5, which the expression products gave a detectable level of activity, have SEQ ID NOs:11 to 14, respectively, and encoding SEQ ID NOs:6 to 9, respectively.

Based on the results in the above experiments, the present inventors found that polypeptides from mammal may require the amino acid sequence of SEQ ID NO:3 (where the symbol "Xaa" meant "glutamine" or "arginine") to express a detectable level of L-asparaginase activity in the expression and assay systems in Experiments 1 and 2, in addition to conventionally known as such amino acid sequences of SEQ ID NOs:1 and 2. The Amino acid sequence of the guinea pig wild-type L-asparaginase contains the SEQ ID NO:3 in the region the amino acids 298–302. Examples of such polypeptides, having all the amino acid sequences of SEQ ID NOs:1 to 3, include those having SEQ ID NOs:4 and 5 from guinea pigs and those having SEQ ID NOs:6 to 9 from human.

Based on the above findings, the present inventors invented the polypeptides having L-asparaginase activity. The following examples explain the present invention, and the techniques used therein are conventional ones used in the art, and of course, they are not restrictive to the present invention:

EXAMPLE A-1

Polypeptides Having L-asparaginase Activity

EXAMPLE A-1(a)

Preparation of Transformant

Ten $\mu$l of 10×PCR buffer, one $\mu$l of 25 mM dNTP mix, one ng of the recombinant DNA pCGPA/WT DNA obtained in Experiment 1-1 as a template, and an adequate amount of oligonucleotides as a sense- and anti-sense-primers synthesized chemically based on the 5'- and 3'-terminal sequences of GPA/WT DNA were placed in 0.5 ml reaction tube. The mixture was mixed with sterilized distilled water to give a total volume of 99.5 $\mu$l, and 0.5 $\mu$l of 2.5 units/$\mu$l AmpliTaq DNA polymerase were further added. The sequence of the sense primer was 5'-GCGAATTCATGGCGCGGCATCA-3'SEQ ID NO:35 which was a nucleotide sequence obtained by adding a cleavage site by a restriction enzyme, Eco RI, to the upstream of the 5'-terminus of GPA/WT DNA. The sequence of the anti-sense primer was 5'-GCAAGCTTTCAGATGGCAGGCGGCAC-3'SEQ ID NO:36, which was complementary to a nucleotide sequence prepared by adding a termination codon to the 3'-terminus of GPA/WT DNA and then adding a cleavage site by a restriction enzyme, Hin dIII, to the downstream. The above mixture was subjected to 40 cycles of successive incubations at 94° C. for one min, at 55° C. for one min, and 72° C. for 3 min to perform PCR. By cleaving the amplified DNA by restriction enzymes Eco RI and Hin dIII, a Eco RI-Hin dIII fragment with a length of about 1.7 kbp was obtained. Twenty-five ng of the DNA was mixed with 10 ng of plasmid vector "pKK223-3", commercialized by Pharmacia LKB Biotechnology AB, Uppsala, Sweden, which had been cleaved by restriction enzymes Eco RI and Hin dIII, and then mixed with the solution I in "LIGATION KIT VERSION 2" commercialized by Takara Shuzo Inc., Tokyo, Japan, in an equal volume of the DNA mixture, followed by incubation at 16° C. for 2 hours to obtain a replicable recombinant DNA, "pKGPA/WT".

Figure 2:
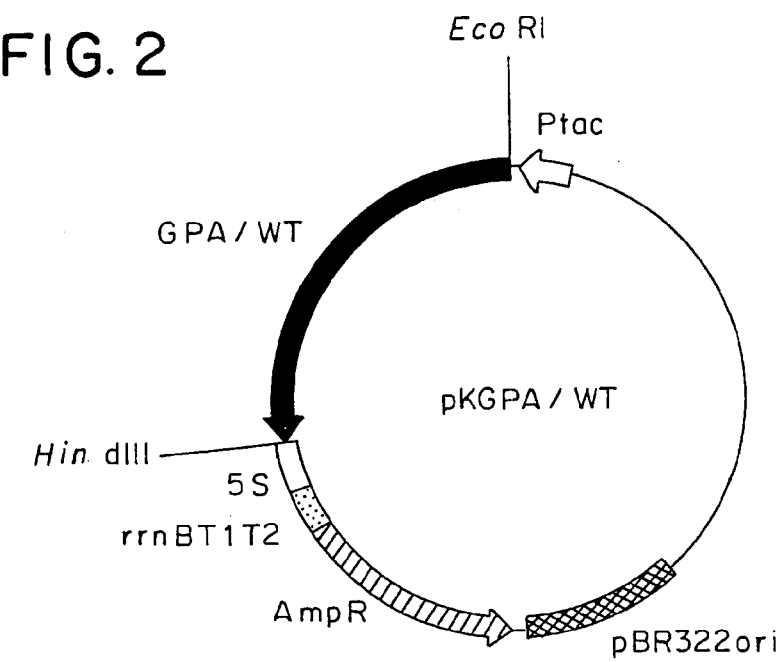
FIG. 2 is a restriction map of the present recombinant DNA pKGPA/WT.

The recombinant DNA pKGPA/WT was introduced into an *Escherichia coli* strain "JM105" by the competent cell method. The resulting transformant "J-GPA/WT" was inoculated to L broth medium (pH 7.2) containing 50 $\mu$g/ml ampicillin and cultured at 37° C. for 18 hours under shaking conditions. The transformants collected by centrifugation from the culture were subjected to a conventional alkcali-SDS method to extract the recombinant DNA pKGPA/WT. As shown in FIG. 2, analysis using an automatic sequencer equipped with a fluorophotometer revealed that GPA/WT DNA of SEQ ID NO:17 ligated to the downstream of a Tac promotor in the direction from the 5'- to 3'-termini. In addition, it was confirmed that a termination codon was ligated to the downstream of GPA/WT DNA without intervening sequences.

EXAMPLE A-1(b)

Production of Polypeptide

The transformant J-GPA/WT was inoculated into L broth medium (pH 7.2), containing 50 $\mu$g/ml ampicillin, and cultured at 37° C. for 18 hours under shaking conditions to obtain a seed culture. Eighteen L of a fresh preparation of the same medium was placed in a 30-L jar fermenter, inoculated with one v/v % of the seed culture, and cultured at 37° C. under aeration-agitation conditions. A portion of the culture was placed in a cuvette with 1-cm in thickness, incubated until the absorbance at a wavelength of 650 nm reached to about 1.5, admixed with IPTG to give a final concentration of 0.1 mM, and incubated for 5 hours. The cells centrifugally collected from the culture were suspended in a mixture solution (pH 7.2) containing 139 mM NaCl, 7 mM $Na_2HPO_4$ and 3 mM $NaH_2PO_4$, and supersonicated to disrupt the cells, followed by centrifuging the resultant to obtain a supernatant.

Ammonium sulfate was added to the supernatant under ice-chilling conditions to give a concentration of 50 w/v % and then dissolved to homogeneity. After standing for several minutes, the precipitates were collected by centrifugation, dissolved in 20 mM Tris-HCl buffer (pH 8.0), and dialyzed against a fresh preparation of the same buffer followed by applying the dialyzed solution to "Q SEPHAROSE FF COLUMN", commercialized by Pharmacia LKB Biotechnology AB, Uppsala, Sweden, equilibrated with the same buffer. After washing sufficiently with the same buffer, the column was fed with a linear gradient buffer of NaCl increasing from 0 M to 0.5 M in 20 mM Tris-HCl buffer (pH 8.0). The fractions eluted at about 0.1–0.3 M NaCl were collected, and the solvent was replaced with 10 mM sodium-phosphate buffer (pH 7.5) while concentrating with membranes. The concentrated solution was then applied to "L-ASPARAGINE AGAROSE",commercialized by Sigma Chemical Co., St. Louis, U.S.A., equilibrated with the same buffer. After washing with the same buffer, 10 mM sodium phosphate buffer (pH 7.5) containing 0.5 M NaCl was fed to the column for elution. The eluted fractions were pooled and concentrated by using a membrane. The concentrate was applied to "HILOAD SUPERDEX 200 COLUMN",commercialized by Pharmacia LKB Biotechnology AB, Uppsala, Sweden, equilibrated with Tris-HCl buffer (pH 8.0) containing 10 v/v % glycerol, and eluted from the column. The eluted fractions, containing substances with a molecular weight of about 300 kDa, were collected to obtain a purified polypeptide with a purity of 90% or more in a yield of about 0.1 mg/ml culture.

EXAMPLE A-1(c)

Physicochemical Property of Polypeptide

The purified polypeptide in the above was analyzed to determine the physicochemical properties: The molecular weight of the purified polypeptide in a native form was determined by gel filtration similarly as in Experiment 1-1(e). The peak for L-asparaginase activity of the eluted fractions was found at a position corresponding to a molecular weight of about 300 kDa. The molecular weight of the purified polypeptide in a dissociated form was determined by SDS-PAGE as used in Experiment 1-1(e). The main band was observed at a position corresponding to a molecular weight of about 50±10 kDa. The results indicate that the purified polypeptide exists in a multimer as a native form. Considering errors in measurement by the above methods and the fact that all the known L-asparaginases from *Escherichia coli* etc., other than mammal, exist in a tetrameric form, it can be estimated that the purified polypeptide exists in a tetrameric form. The method as used in Experiment 1-1(d) confirmed that the purified polypeptide has an L-asparaginase activity.

EXAMPLE A-2(a)

Preparation of Transformant

FIG. 3 summarizes the procedures to prepare transformants. PCR was performed under the same conditions as used in Example A-1(a) except for the nucleotide sequences of a sense- and anti-sense-primers. As the sense- and anti-sense-primers, oligonucleotides with the nucleotide sequences of 5'-GTGAATTCGGAGGTTCAGATGGCGCGCGCATCA-3' SEQ ID NO:37 and 5'-CTGCGGCCGCTCAGATGGCAGGCGGCAC-3' SEQ ID NO:38 were respectively used. The DNA thus amplified was cleaved by restriction enzymes Eco RI and Not I to obtain an about 1.7 kbp Eco RI-Not I fragment. Seventy ng of the DNA fragment was mixed with 50 ng of a plasmid vector, "pBPV",commercialized by Pharmacia LKB Biotechnology AB, Uppsala, Sweden, cleaved in advance by restriction enzymes Xho I and Not I, and 25 ng of each of 4 oligonucleotides as linkers with nucleotide sequences of 5'-TCGAGCCACCATGAAGTGTTCGTGGGTTATT-3' SEQ ID NO:39, 5'-TTCTTCCTGATGGCCGTAGTGACAGGAGTG-3' SEQ ID NO:40, 5'-AATTCACTCCTGTCACTACGGCCATCAGGA-3' SEQ ID NO:41, and 5'-AGAAAATAACCCACGAACACTTCATGGTGGC-3' SEQ ID NO:42. The oligonucleotides for linkers were synthesized in a usual manner and used after reacted with T4 polynucleotide kinase, commercialized by Pharmacia LKB Biotechnology AB, Uppsala, Sweden, and purified by ethanol-precipitation. To the DNA mixture was added the solution I in "LIGATION KIT VERSION 2",commercialized by Takara Shuzo, Tokyo, Japan. The mixture was incubated at 16° C. for 2 hours to obtain a replicable recombinant DNA "pBIgGPA/WT".

Figure 4:
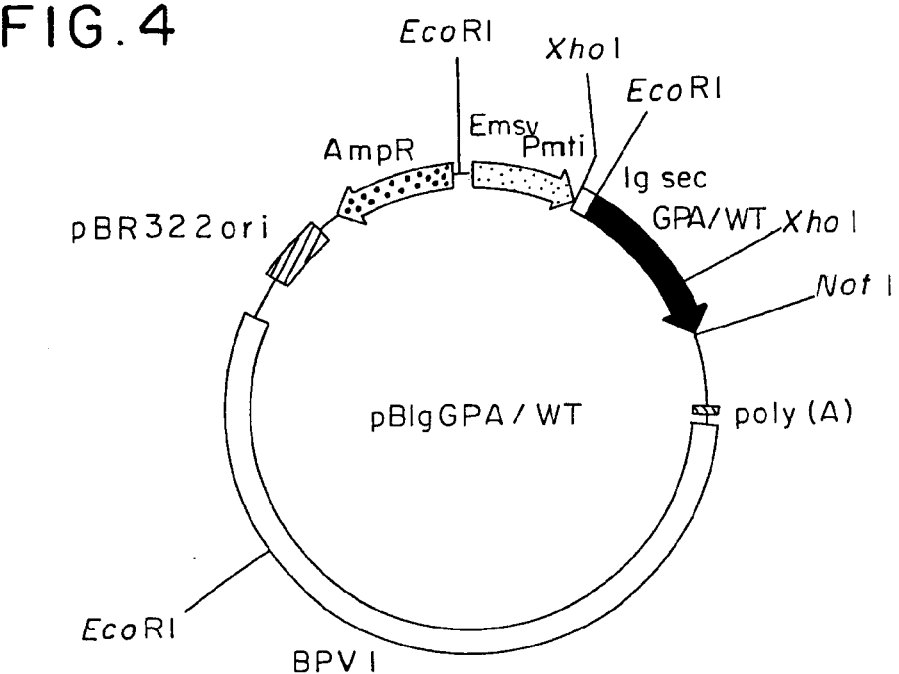
FIG. 4 is a restriction map of the present recombinant DNA pBIgGPA/WT.
Figure 5:
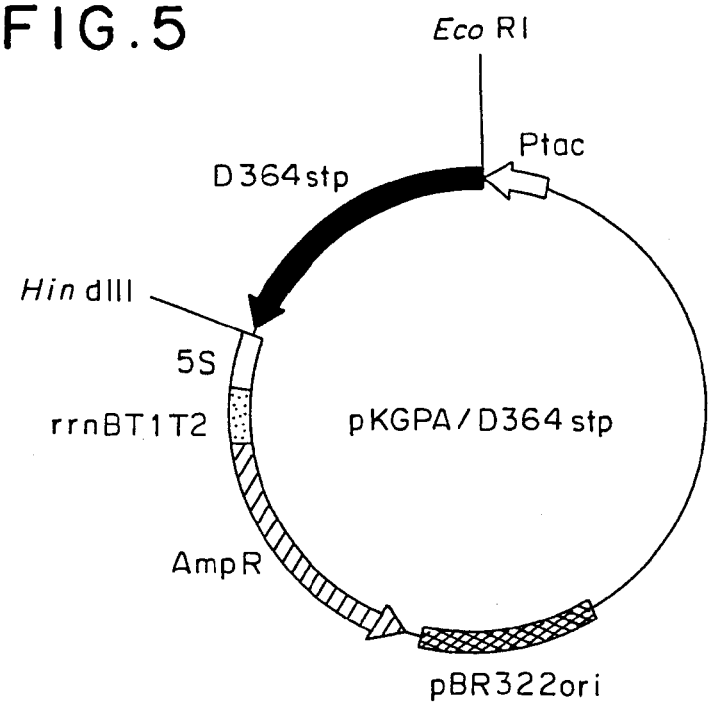
FIG. 5 is a restriction map of the present recombinant DNA pKGPA/D364stp.
Figure 6:
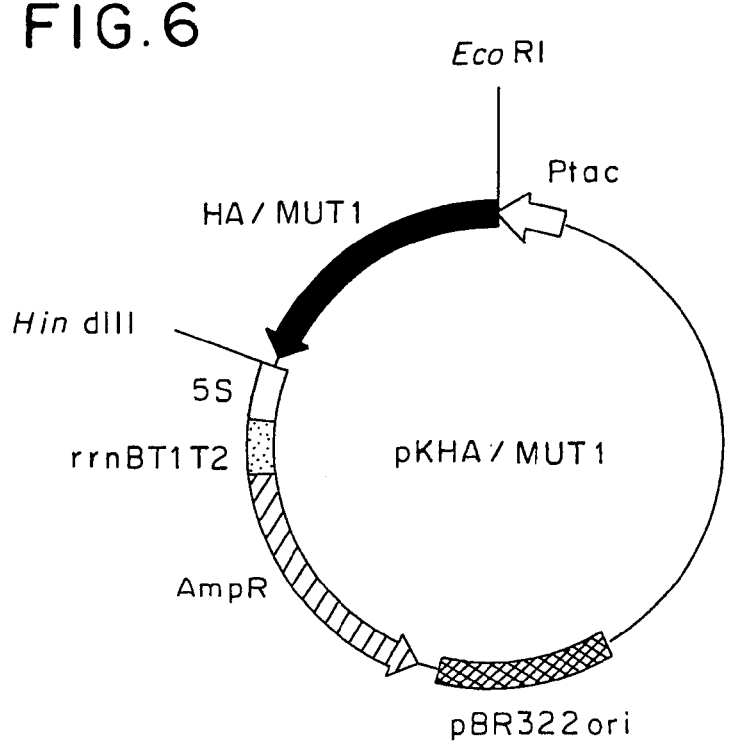
FIG. 6 is a restriction map of the present recombinant DNA pKHA/MUT1.
Figure 7:
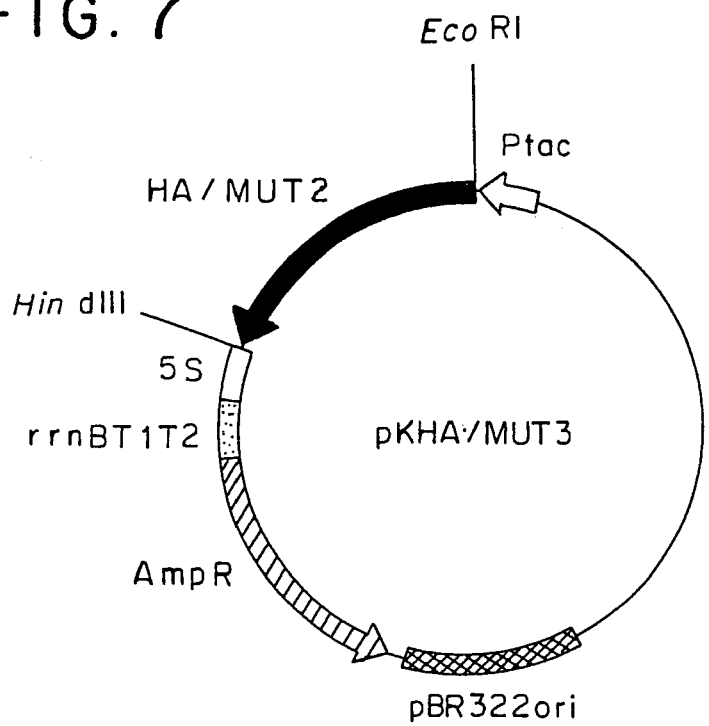
FIG. 7 is a restriction map of the present recombinant DNA pKHA/MUT2.
Figure 8:
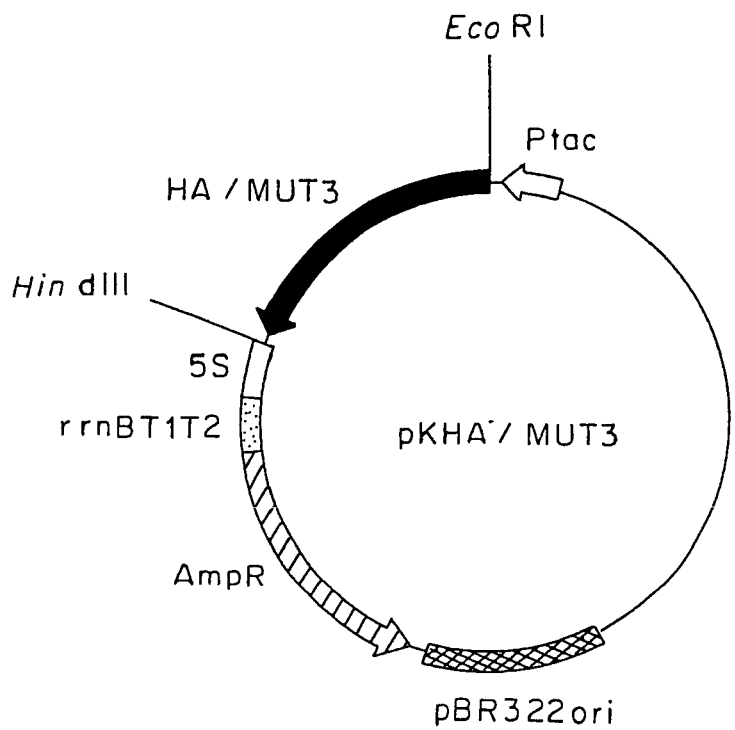
FIG. 8 is a restriction map of the present recombinant DNA pKHA/MUT3.
Figure 9:
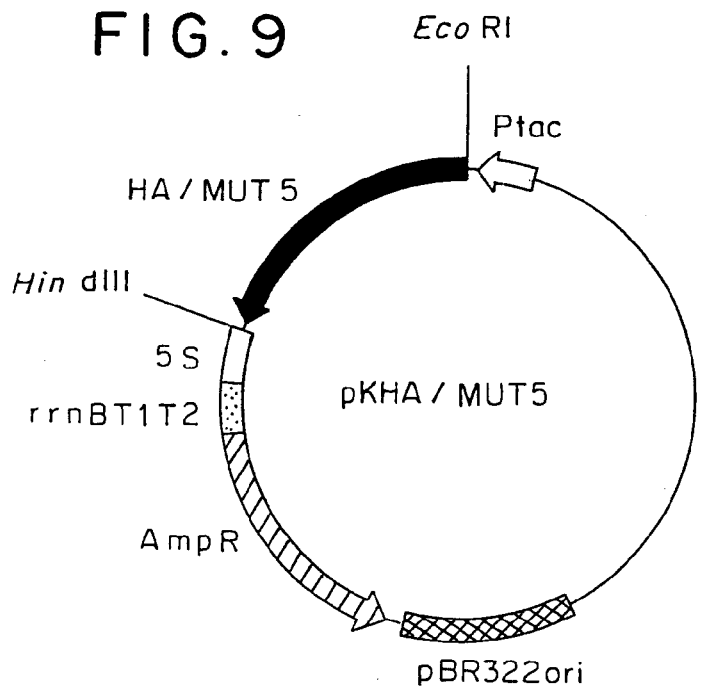
FIG. 9 is a restriction map of the present recombinant DNA pKHA/MUT3.
Figure 10:
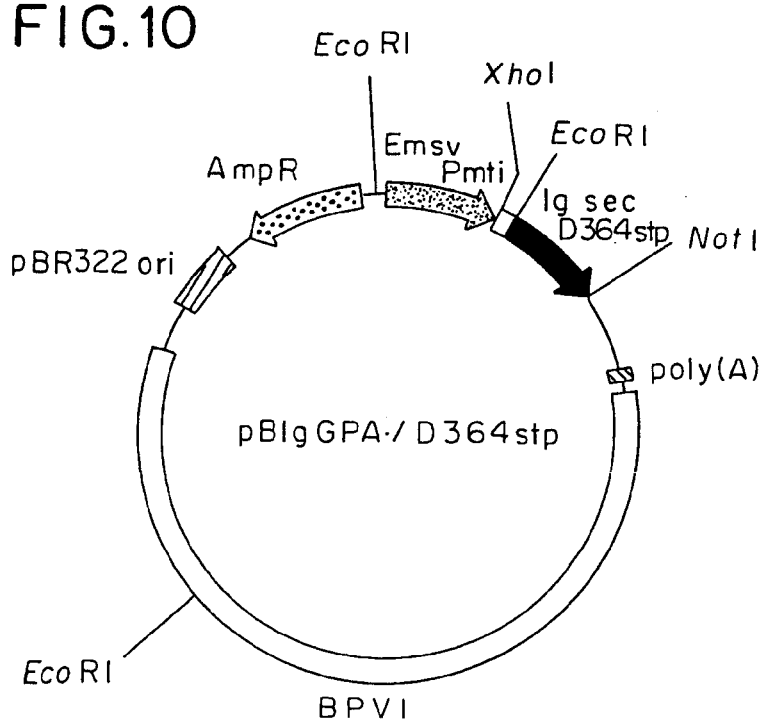
FIG. 10 is a restriction map of the present recombinant DNA pBIgGPA/D364stp.
Figure 11:
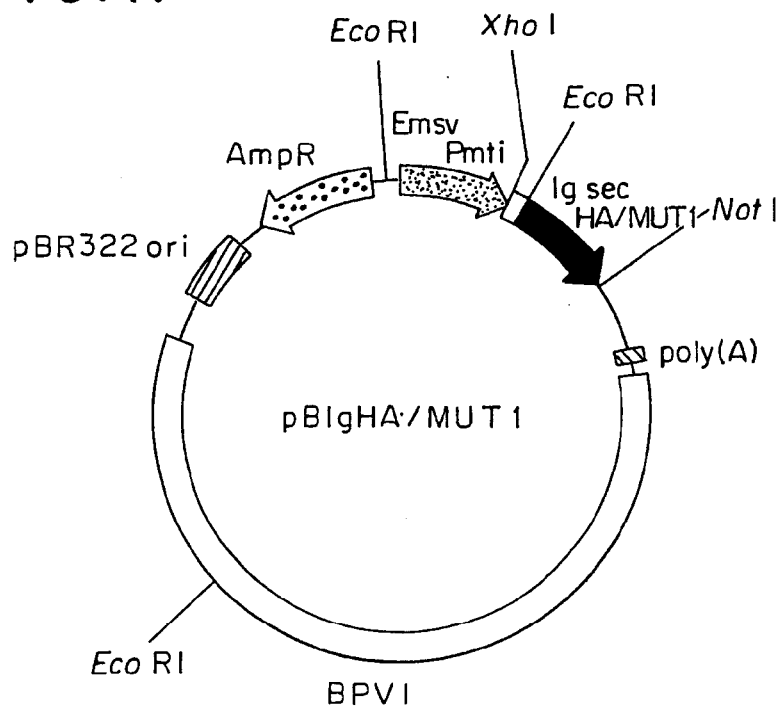
FIG. 11 is a restriction map of the present recombinant DNA pBIgHA/MUT1.
Figure 12:
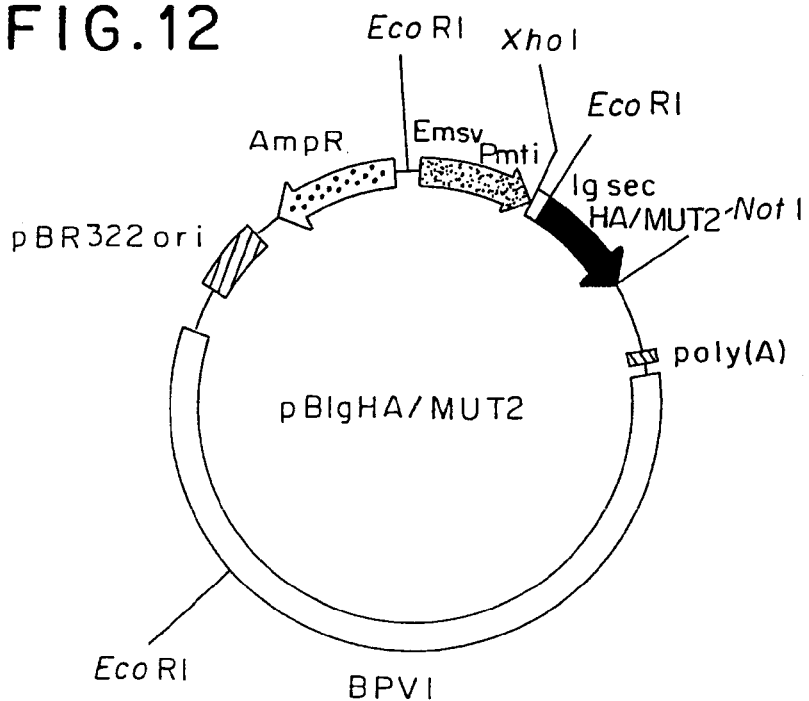
FIG. 12 is a restriction map of the present recombinant DNA pBIgHA/MUT2.
Figure 13:
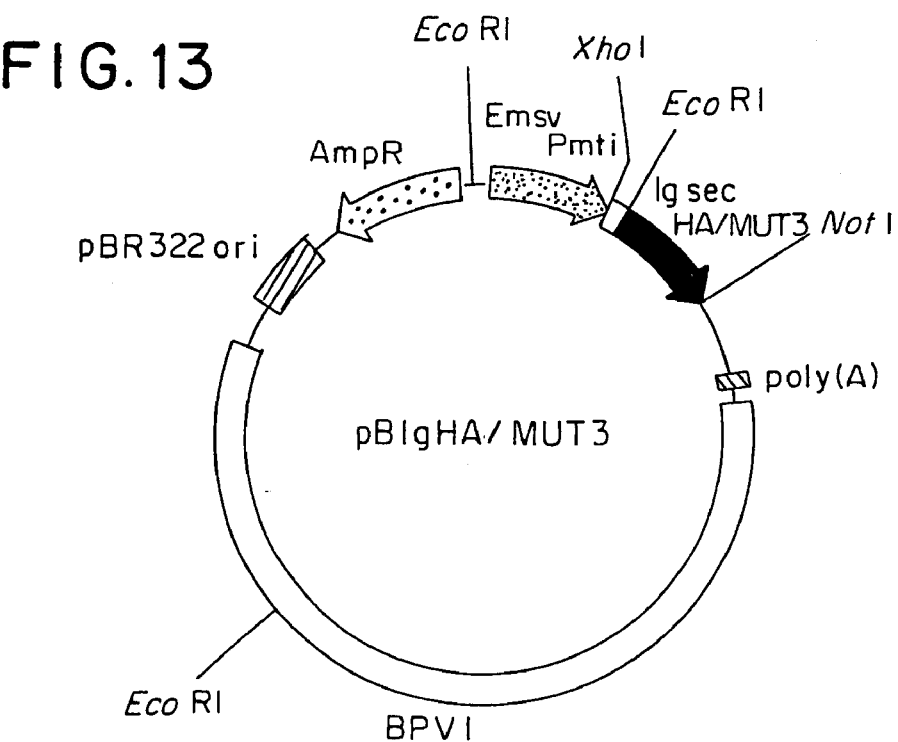
FIG. 13 is a restriction map of the present recombinant DNA pBIgRA/MUT3.
Figure 14:
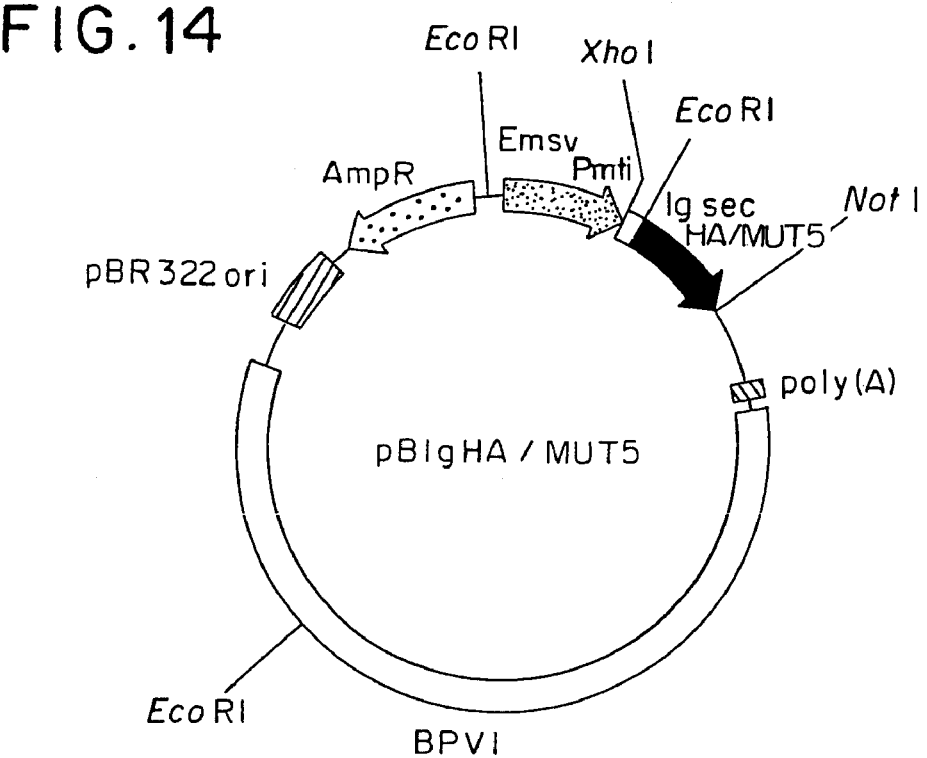
FIG. 14 is a restriction map of the present recombinant DNA pBIgHA/MUT4.

The recombinant DNA pBIgGPA/WT was introduced into-an *Escherichia Coli* HB101 strain by the competent cell method. The transformant thus obtained was inoculated into L broth medium (pH 7.2) containing 50 μg/ml ampicillin followed by cultivation at 37° C. for 18 hours under shaking conditions. The transformants, collected by centrifuging the resulting culture, were subjected to a conventional alkali-SDS method to extract the recombinant DNA pBIgGPA/WT. The nucleotide sequence analysis using an automatic sequencer confirmed that the recombinant DNA pBIgGPA/WT had the structure in FIG. 4: A DNA encoding a polypeptide containing a signal sequence for immunoglobulin secretion, as shown by D. F. Stern et al. in "Science", Vol. 235, pp. 321–324 (1984), i.e., "Ig sec DNA" was ligated to the downstream of a region for transcriptional regulation, comprising an enhancer derived from long terminal repeats of Moloney Mouse Sarcoma Virus (Emsv), and a promotor derived from Mouse metallothionein I gene (Pmti). Furthermore, GPA/WT DNA was ligated in the same frame to the downstream of the Ig sec DNA in the direction from the 5'- to 3'-termini of GPA/WT DNA. It was also confirmed that a termination codon exists in the 3'-terminus of GPA/WT DNA without intervening sequences.

The recombinant DNA pBIgGPA/WT was introduced into a cell line C127 (ATCC CRL-1616), derived from a mouse, by using a LIPOFECTIN® reagent commercialized by Life Technologies, Inc., Gaitherburg, U.S.A., according to the attached protocol. The transformants with the recombinant DNA were selected based on the lack of proliferation-regulatory ability, i.e., focus-forming ability, as a first selection. The cells around those containing foci were collected using sterilized filter papers and subjected to a conventional limiting dilution method to form single cells which were then selected depending on the productivity of L-asparaginase, as final selection. Thus, a transformant, "C-GPA/WT", was obtained.

EXAMPLE A-2(b)

Production of Polypeptide

The transformant C-GPA/WT was inoculated into a well of "3046", a plastic multiwell plate with 6 wells, 3.5 cm in diameter, commercialized by Becton Dickinson Labware, New Jersey, U.S.A., with DME medium containing 10 v/v % bovine fetal serum, and cultured to be confluent as a seed culture. Some of the cells, scraped by treatment with trypsin, were inoculated as seed cells into each of the multiwell plates which were charged with the fresh preparation of the same medium and cultured. After repeating manipulations similarly as in the above and with scale up to increase the cell number, the cells were subjected to a conventional continuous culture using 50 of 150 $cm^2$ culture flasks. The resulting culture supernatants of a volume of 100 1 was collected and treated with similar methods for treating the supernatant from the cell-disruptants in Example A-1(b): salting out with ammonium sulfate, the chromatography of the solution of the precipitates using Q SEPHAROSE FF COLUMN, the chromatography of the eluted fractions using L-ASPARAGINE AGAROSE, and the chromatography of the eluted fractions using HILOAD SUPERDEX 200 COLUMN. Consequently, a purified polypeptide with a purity of 90% or more was obtained in a yield of about one μg/ml-culture.

EXAMPLE A-2(c)

Physicochemical Property of Polypeptide

By testing similarly as in Example A-1(c), it was confirmed that the purified polypeptide thus obtained had equivalent physicochemical properties with the that obtained in Example A-1(b).

EXAMPLE A-3(a)

Preparation of Transformant

PCRs were performed under the same conditions in Example A-1(a) except for the template and the sense- and anti-sense-primers. The DNA thus obtained were treated similarly as in Example A-1(a) to prepare recombinant DNAs, "pKGPA/D364stp", "pKHA/MUT1", "pKHA/MUT2", "pKHA/MUT3" and "pKHA/MUT5". Table 5 summarizes template DNAs and nucleotide sequences of a sense-and anti-sense-primers which were used to prepare the each recombinant DNAs. By sequencing similarly as in Example A-1(a), the structures of these recombinant DNAs were confirmed as shown in FIGS. 5 to 9.

TABLE 5

| Recombinant DNA | Template DNA | Nucleotide sequences of sense (upper line) and anti-sense (lower line) primers * |
|---|---|---|
| pKGPA/D364stp | pCGPA/D364stp | 5'-GCGAATTC*ATGGCGCGCGCATCA*-3'(SEQ ID NO:35)<br>5'-GCAAGCTTTCATGCCGTGGGCAGTGT-3'(SEQ ID NO:43) |
| pKHA/MUT1 | pCHA/MUT1 | 5'-GCGAATTC*ATGGCGCGCGCGGTG*-3'(SEQ ID NO:44)<br>5'-GCAAGCTTTCACACCGAGGGTGGCGT-3'(SEQ ID NO:45) |
| pKHA/MUT2 | pCHA/MUT2 | the same as used for pKHA/MUT1 preparation<br>the same as used for pKHA/MUT1 preparation |
| pKHA/MUT3 | pCHA/MUT3 | the same as used for pKHA/MUT1 preparation<br>the same as used for pKHA/MUT1 preparation |
| pKHA/MUT5 | pCHA/MUT5 | the same as used for pKHA/MUT1 preparation<br>the same as used for pKHA/MUT1 preparation |

*) Italics in the upper line in each column mean the 5'-terminal nucleotide sequence of a DNA encoding L-asparaginase, and those in the lower line mean the complementary sequence to the 3'-terminus of the DNA, wherein the L-asparaginese originates from a guinea pig or human.

The recombinant DNAs were treated according to the methods as in Example A-1(a) to obtain transformants, "J-GPA/D364stp", "J-HA/MUT1", "J-HA/MUT2T", "J-HA/MUT3" and "J-HA/MUT5".

EXAMPLE A-3(b)

Production of Polypeptide

The transformants obtained in Example A-3(a) were treated according to the methods similarly as in Example A-1(b): cultivation, disrupting the resulting cells, the precipitations of the cell-disruptants with ammonium sulfate, the chromatography of the precipitate solutions using Q SEPHAROSE FF COLUMN, and the chromatography of the eluted fractions using L-ASPARAGINE AGAIROSE in that order. The eluted fractions thus obtained were concentrated using membranes similarly as in Example A-1(b) followed by subjecting the chromatography using HILOAD SUPERDEX 200 COLUMN to collect the eluted fractions with a molecular weight of about 140 kDa. Each system yielded the purified polypeptide with a purity of 90% or more in a yield of about 0.1 mg/ml-culture. These purified polypeptides were analyzed by the methods as in Example A-1(c) to examine their physicochemical properties. Table 6 shows the results combined with those in Example A-1(c).

TABLE 6

| Transformant, producing the polypeptide | Molecular weight (kDa) *1 | Molecular weight (kDa) *2 | L-asparaginase activity |
|---|---|---|---|
| J-GPA/WT | about 300 | about 50 ± 10 | + |
| J-GPA/D364stp | about 140 | about 40 | + |

TABLE 6-continued

| Transformant, producing the polypeptide | Molecular weight (kDa) *1 | Molecular weight (kDa) *2 | L-asparaginase activity |
|---|---|---|---|
| J-HA/MUT1 | about 140 | about 40 | + |
| J-HA/MUT2 | about 140 | about 40 | + |
| J-HA/MUT3 | about 140 | about 40 | + |
| J-HA/MUT5 | about 140 | about 40 | + |

Note) The symbols "*1" and "*2" mean that the value was determined by gel filtration, and the value was determined by SDS-PAGE, respectively.

Table 6 indicates that all of the present polypeptides, expressed in *Escherichia coli* and purified, expressed an L-asparaginase activity. Furthermore, table 6 indicates the that the polypeptides formed tetramers.

EXAMPLE A-4(a)

Preparation of Transformants

PCRs were performed under the same conditions in Example A-1(a) except for the template and the sense- and anti-sense-primers. DNAs thus obtained were ligated with the same linkers as used in Example A-2(a) under the same conditions as in Example A-2(a) to obtain recombinant DNAs, "pBIgGPA/D364stp", "pBIgHA/MUT1", "pBIgHA/MUT2", "pBIgHA/MUT3" and "pBIgHA/MUT5". Table 7 summarizes template DNAs and nucleotide sequences of sense- and anti-sense-primers which were used to prepare the each recombinant DNAs. By sequencing similarly as in Example A-1(a), the structures of these recombinant DNAs were confirmed as shown in FIGS. 10 to 14.

TABLE 7

| Recombinant DNA | Template DNA | Nucleotide sequences of sense (upper line) and anti-sense (lower line) primers * |
|---|---|---|
| pBIgGPA/D364stp | pCGPA/D364stp | 5'-GTGAATTCGGAGGTTCAGA*TGGCGCGCGCATCA*-3'(SEQ ID NO:37)<br>5'-CTGCGGCCGCTCAT*GCCGTGGGCAGTG*-3'(SEQ ID NO:46) |
| pBIgHA/MUT1 | pCHA/MUT1 | 5'-CTGAATTCGGAGGTTCAGA*TGGCGCGCGCGGTG*-3'(SEQ ID NO:47)<br>5'-CTGCGGCCGCTCAC*ACCGAGGGTCGCG*-3'(SEQ ID NO:48) |

TABLE 7-continued

| Recombinant DNA | Template DNA | Nucleotide sequences of sense (upper line) and anti-sense (lower line) primers * |
|---|---|---|
| pBIgHA/MUT2 | pCHA/MUT2 | the same as used for pBIgHA/MUT1 preparation<br>the same as used for pBIgHA/MUT1 preparation |
| pBIgHA/MUT3 | pCHA/MUT3 | the same as used for pBIgHA/MUT1 preparation<br>the same as used for pBIgHA/MUT1 preparation |
| pBIgHA/MUT5 | pCHA/MUT5 | the same as used for pBIgHA/MUT1 preparation<br>the same as used for pBIgHA/MUT1 preparation |

Note) *:
Italics in the upper line in each column mean the 5'-terminal nucleotide sequence of a DNA encoding L-asparaginase, and those in the lower line mean the complementary sequence to the 3'-terminus of the DNA, wherein the L-asparaginese originates from a guinea pig or human.

The recombinant DNAs thus obtained were treated similarly as in Example A-2(a) to obtain transformants, "C-GPA/D364stp", "C-HA/MUT1", "C-HA/MUT2", "C-HA/MUT3" and "C-HA/MUT5".

EXAMPLE A-4(b)

Production of Polypeptide

The transformants obtained in Example A-4(a) were cultured according to the methods as in Example A-2(b), and the resulting culture supernatants were treated with similar methods for treating the supernatants from the cell-disruptants in Example A-1(b): the precipitations of culture supernatants with ammonium sulfate, the chromatography of the precipitate solutions using Q SEPHAROSE FF COLUMN, and the chromatography of the eluted fractions using L-ASPARAGINE AGAROSE in that order. The eluted fractions thus obtained were concentrated using membranes similarly as in Example A-1(b) followed by subjecting the chromatography using HILOAD SUPERDEX 200 COLUMN to collect the eluted fractions with a molecular weights of about 140kDa. Each of these systems yielded the purified polypeptide with a purity of 90% or more in a yield of about one µg/ml-culture. These purified polypeptides were analyzed by the methods as in Example A-1(c) to examine their physicochemical properties. Table 8 shows the results combined with those in Example A-3.

TABLE 8

| The polypeptide-producing transformant | Molecular weight (kDa) *1 | Molecular weight (kDa) *2 | L-asparaginase activity |
|---|---|---|---|
| J-GPA/WT | about 300 | about 50 ± 10 | + |
| J-GPA/D364stp | about 140 | about 40 | + |
| J-HA/MUT1 | about 140 | about 40 | + |
| J-HA/MUT2 | about 140 | about 40 | + |
| J-HA/MUT3 | about 140 | about 40 | + |
| J-HA/MUT5 | about 140 | about 40 | + |

Note) The symbols "*1" and "*2" mean that the value was determined by gel filtration, and the value was determined by SDS-PAGE, respectively.

Table 8 indicates that all of the present polypeptides, expressed in mammalian cells and purified, expressed an L-asparaginase activity. Furthermore, table 8 indicates the polypeptides formed tetramers.

As shown in above Example A, each of the polypeptides according to the present invention expresses an L-asparaginase activity. Therefore, the present agent for susceptive diseases hydrolyze L-asparagine in patients to exert therapeutic and preventive effects on L-asparaginase-susceptive diseases when administered to human. The wording "susceptive diseases" as referred in the present specification means diseases in general which are caused by the existence of tumor cells dependent on L-asparagine: For example, leukemias such as acute leukemia, an acute transformation of chronic leukemia and T-lymphocytic leukemia, and malignant tumors such as Hodgkin's diseases and non-Hodgkin's diseases. The present agent for susceptive diseases possesses thus the uses as anti-tumor agents for treating and/or preventing such susceptive diseases as above. Although it varies dependently on the types of agents used for such purposes and susceptive diseases to be treated, the present agent is generally processed into an agent in the form of a liquid, a paste or a solid which contains the polypeptides in an amount of 0.000001–100 w/w %, preferably, 0.0001–100 w/w %, on a dry solid basis.

The present agent can be used intact or processed into compositions by mixing with one or more selected from the group consisting of physiologically-acceptable carriers, excipients, solvents, buffers and stabilizers, and further, if necessary, other biologically-active substances and other agents. For example, "Iyakuhin-Tenkabutsu-Jiten (The Dictionary of Pharmaceutical Excipients)" (1994), edited by Japan Pharmaceutical Excipients Council, Tokyo, Japan, published by Yakujinippo LTD., Tokyo, Japan and "Iyakuhin-Tenkabutsu-Jiten-Tsuiho 1995 (Supplement for The Dictionary of Pharmaceutical Excipients)" (1995), edited by Japan Pharmaceutical Excipients Council, Tokyo, Japan, published by Yakujinippo LTD., Tokyo, Japan, mention the embodiments of such carriers, excipients, solvents, buffers and stabilizers. Examples of such other biologically-active substances and other agents include interferon-α, interferon-β, interferon-γ, interleukin 1, interleukin 2, interleukin 3, TNF-α, TNF-β, GM-CSF, carboquone, cyclophosphamide, aclarbicin, thiotepa, busulfan, ancitabine, cytarabine, fluorouracil, 5-fluoro-1-(tetrahydro-2-furyl)uracil, methotrexate, actinomycin D, chromomycin A3, daunorubicin, doxorubicin, bleomnycin, mercaptopurine, prednisolone, mitomycin C, vincristine, vinblastine, radio gold colloidal, Krestin®, picibanil, lentinan and Maruyama vaccine.

The present agent for susceptive diseases includes those in a unit dose form which means a physically separated and formed medicament suitable for administration, and contains the polypeptides in a daily dose or in a dose from ¹⁄₄₀ to several folds (up to 4 folds) of the daily dose. Examples of such medicaments are injections, liquids, powders, granules, tablets, capsules, sublinguals, ophthalmic solutions, nasal drops and suppositories.

The present agent can be administered to patients orally or parenterally. In both administrations, the agent exerts a satisfactory effect in the treatment and/or the prevention for the susceptive diseases. Although it varies dependently on the types of susceptive diseases and their symptoms, the agent can be orally administered to patients or parenterally administered to patients' intradermal tissues, subcutaneous tissues, muscles, and veins at a dose as amounts of the polypeptides in the range of about 0.1μg–500mg/shot, preferably, about 0.1–100 mg/shot, 1–4 times/day or 1–7 times/week, for one day to one year. The present agent for susceptive diseases further includes the forms by applying gene therapy. When a transformant into which the DNAs encoding the polypeptides of this invention are introduced are administered to patients to express in them, they exert equivalent effects as above administrations. For example, "Jikken-Igaku Bessatsu, Bio-manual Up Series, Idenshi-Chiryo-No-Kisogijutsu (Basic Techniques for Gene Therapy)" (1996), edited by Takashi SHIMADA, Izumi SAITO and Takaya OZAWA, published by Yodosha, Tokyo, Japan, details the general procedures for the gene therapy.

The biological activities and acute toxicity of the present polypeptides are explained based on Experiment 3 and 4 below, respectively.

EXPERIMENT 3

Biological Activity

EXPERIMENT 3-1

Antitumor Effect in vitro

A human histocytic lymphoma cell line U937 (ATCC CRL-1593), and a cell line Molt4 (ATCC CRL-1582), derived from human T lymphoblasts, were subcultured in RPMI 1640 medium containing 10v/v % bovine fetal serum. The cells collected by centrifugation from each subculturing system in logarithmic phase were suspended in the same medium to give a concentration of $2 \times 10^5$ cells/ml. Every one ml of the each cell suspension was charged into each of 13 wells of multiwell plates with 24 wells, "3047", commercialized by Becton Dickinson Labware, New Jersey, U.S.A. After each of dilutions of 12 types of the purified polypeptides prepared in Example A-1 to A-4 with PBS was further charged into the each well, the cells were cultured at 37° C. for 72 hours in a 5 v/v %. $CO_2$ incubator. The final concentration of each of the purified polypeptides was one unit/ml as an L-asparaginase activity. As a control, after charged with equivalent volume of P8S, the cells were cultured correspondingly. The cells were collected after the cultivation to stain cells died with trypan blue. Cell survival ratio in each systems with the purified polypeptides was compared with that in the control. All of the cell survival ratios with the purified polypeptides were significantly lower than that in the control. These results indicate that all of the present polypeptides, obtained in Examples A-1 to A-4, have cytotoxicity to U937 and Molt4.

EXPERIMENT 3-2

Antitumor Effect in vivo

For model mice were used C3H mice wherein a mouse lymphoma cell line 6C3HED, registered in Cell Resource Center for Biomedical Research, Institute of Development Aging and Cancer, Tohoku University, Sendai, Japan, was transplanted with passages by subcutaneous injections at their sides in a range of $1 \times 10^7$ cells/body every 8 days in usual manner. To the model mice were administered the purified polypeptides obtained in Example A-1 to A-4 in the range of 400 unit/body by venoclyses every day from fourth to seventh days after transplanted with the cells. Dimensions of the tumors were observed with naked eyes on fourth and eighth day after the transplantations. The purified polypeptides were administered after diluted with 0.15 M NaCl and filtrated with membrane filters, 0.45 μm in pore size, commercialized by Millipore Corp., Bedford, U.S.A. As a control, 0.15 M NaCl was treated correspondingly. While significant enlargements of the tumors were observed in the control, significant involutions or disappearances of the tumors were observed in mice administered with the polypeptides. These results indicates that all of the present polypeptides, obtained in Examples A-1 to A-4, are able to cure the tumors of model mice.

EXPERIMENT 4

Acute Toxicity

The purified polypeptides obtained in Examples A-1 to A-4 were separately administered to 8-week-old mice percutaneously, perorally or intraperitoneally according to conventional manner. The $LD_{50}$ of all the polypeptides was about 100 mg/kg or higher independently of the administration routes. These results evidenced that the present polypeptides could be safely incorporated into pharmaceuticals for administering human.

The following examples explain the present agent for susceptive diseases.

EXAMPLE B-1

Solution

The purified polypeptides obtained in Examples A-1 to A-4 were separately dissolved to give a concentration of 0.1 mg/ml in physiological saline containing one w/v % human serum albumin as a stabilizer, and sterilized with membrane filters according to conventional manner to obtain solutions.

All of the products have satisfactory stabilities and can be used as injections, ophthalmic solutions, collunarium in the treatment and/or the prevention of susceptive diseases including a malignant tumor, acute leukemia, malignant lymphoma, an acute transformation of chronic leukemia, T-lymphocytic leukemia.

EXAMPLE B-2

Solution

The purified polypeptides obtained in Examples A-1 to A-4 were separately dissolved to give a concentration of 0.1 mg/ml in physiological saline containing one w/v % glycerol as a stabilizer, and sterilized with membrane filters according to conventional manner to obtain solutions.

All of the products have satisfactory stabilities and can be used as injections, ophthalmic solutions, collunarium for the treatment and/or the prevention of susceptive diseases including a malignant tumor, acute leukemia, malignant lymphoma, an acute transformation of chronic leukemia and T-lymphocytic leukemia.

EXAMPLE B-3

Dry Injection

The purified polypeptides obtained in Examples A-1 to A-4 were separately dissolved to give a concentration of 50 mg/ml in physiological saline containing one w/v % purified gelatin as a stabilizer, and the solutions were sterilized with membrane filters according to conventional manner. One ml aliquots of the sterilized solutions were distributed to vials, lyophilized and cap sealed.

All of the products have satisfactory stabilities and can be used as dry injections for the treatment and/or the prevention of susceptive diseases including a malignant tumor, acute leukemia, malignant lymphoma, an acute transformation of chronic leukemia and T-lymphocytic leukemia.

EXAMPLE B-4

Ointment

"HI-BIS-WAKO 104", a carboxyvinyl polymer commercialized by Wako Pure Chemicals, Tokyo, Japan, and a purified trehalose were dissolved in sterilized distilled water to give concentrations of 1.4 w/w % and 2.0 w/w %, respectively, and the purified polypeptides obtained in Examples A-1 to A-4 were separately mixed to homogeneity in the solutions followed by adjusting the pH of the resulting solutions to pH 7.2 to obtain pastes containing about one mg/g of the polypeptides.

All of the products have satisfactory spreadabilities and stabilities, and can be used as ointments for treating and/or preventing susceptive diseases including a malignant tumor, acute leukemia, malignant lymphoma, an acute transformation of chronic leukemia and T-lymphocytic leukemia.

EXAMPLE B-5

Tablet

Any one of the purified polypeptides obtained in Examples A-1 to A-4 and LUMIN, i.e. [bis-4-(1-ethylquinoline)][γ-4'-(1-ethylquinoline] pentamethionine cyanine, as a cell activator were mixed to homogeneity with "FINETOSE®", an hydrous crystalline α-maltose commercialized by Hayashibara Co., Ltd., Okayama, Japan, and the mixtures were tabletted by tabletting machine to obtain tablets, about 200 mg weight each, containing the polypeptide and the LUMIN, about 5 mg each.

All of the products have satisfactory swallowing abilities, stabilities and cell activating activities, and can be used for treating and/or preventing susceptive diseases including a malignant tumor, acute leukemia, malignant lymphoma, an acute transformation of chronic leukemia and T-lymphocytic leukemia.

A The present invention is based on the findings of polypeptides which originate from mammal, having L-asparaginase activity. The polypeptides are substances which have revealed amino acid sequences totally, and stable activities to hydrolyze L-asparagine. Therefore, the polypeptides exert satisfactory effects in the treatment and/ or the prevention for diseases caused by tumor cells dependent on L-asparagine.

The polypeptides originate from mammal, so that they have low antigenicities to human and don't cause serious side effects even when administered in large amounts or continuously. Therefore, the polypeptides have the advantage that they can exert desired effects without restricted controls on patients'sensitivities.

The polypeptides thus valuable can be produced in desired amounts using the present DNAs encoding them.

Thus, the present invention is a significant invention which has a remarkable effect and gives a great contribution to this field.

While there has been described what is at present considered to be the preferred embodiments of the present invention, it will be understood the various modifications may be made therein, and it is intended to cover in the appended claims all such modifications as fall within the true spirits and scope of the invention.

What is claimed is:

1. An isolated DNA molecule encoding a polypeptide having L-asparaginase activity, wherein said DNA molecule consists of either:

(a) a nucleotide sequence consisting of a part of SEQ ID NO:14 with the remainder of SEQ ID NO:14 substituted with the corresponding part of SEQ ID NO:10; or (b) a fragment of the nucleotide sequence of (a), which fragment contains a part of SEQ ID NO:14 and a part of SEQ ID NO:10, and which encodes a polypeptide having L-asparaginase activity.

2. A self-replicable vector, comprising an isolated DNA molecule encoding the polypeptide having L-asparaginase activity according to claim 1.

3. A host cell transformed by the self-replicable vector according to claim 2.

4. The host cell according to claim 3, wherein said host cell is selected from the group consisting of prokaryotic and eukaryotic cells.

5. The host cell according to claim 3, wherein said host cell is *Escherichia coli*.

6. The host cell according to claim 3, wherein said host cell is a mouse cell.

7. The self-replicable vector according to claim 2, which is a plasmid vector.

8. The self-replicable vector according to claim 2, further comprising one or more promoters selected from the group consisting of metallothionein and Tac promoters.

9. A host cell transformed with a DNA molecule according to claim 1.

10. The host cell according to claim 9, wherein said host cell is a member selected from the group consisting of prokaryotic and eukaryotic cells.

11. The host cell according to claim 9, wherein said host cell is *Escherichia coli*.

12. The host cell according to claim 9, wherein said host cell is a mouse cell.

13. A process for preparing a polypeptide having L-asparaginase activity, comprising:

expressing a DNA molecule encoding the polypeptide according to claim 1; and collecting the expressed polypeptide.

14. The process according to claim 13, wherein the expressing step comprises culturing a host cell transformed with the DNA molecule encoding the polypeptide.

15. The process according to claim 13, wherein the collecting step comprises one or more techniques selected from the group consisting of salting out, dialysis, filtration, concentration, gel filtration chromatography, ion-exchange chromatography, affinity chromatography, hydrophobic chromatography, isoelectric focusing and gel electrophoresis.

16. An isolated DNA molecule encoding a polypeptide having L-asparaginase activity, wherein the DNA molecule consists of a fragment of the nucleotide sequence of SEQ ID NO:17, wherein said fragment is a 5'-terminal part of SEQ ID NO:17 consisting of over 1,011 nucleotides and encodes a polypeptide having L-asparaginase activity.

17. A self-replicable vector, comprising an isolated DNA molecule encoding the polypeptide having L-asparaginase activity according to claim 16.

18. A host cell transformed by the self-replicable vector according to claim 17.

19. The host cell according to claim 18, wherein said host cell is a member selected from the group consisting of prokaryotic and eukaryotic cells.

20. The host cell according to claim 18, wherein said host cell is *Escherichia coli*.

21. The host cell according to claim 18, wherein said host cell is a mouse cell.

22. The self-replicable vector according to claim 17, which is a plasmid vector.

23. The self-replicable vector according to claim 17, further comprising one or more promoters selected from the group consisting of metallothionein and Tac promoters.

24. A host cell transformed with a DNA molecule according to claim 16.

25. The host cell according to claim 24, wherein said host cell is a member selected from the group consisting of prokaryotic and eukaryotic cells.

26. The host cell according to claim 24, wherein said host cell is *Escherichia coli*.

27. The host cell according to claim 24, wherein said host cell is a mouse cell.

28. A process for preparing a polypeptide having L-asparaginase activity, comprising:

expressing a DNA molecule encoding the polypeptide according to claim 16; and collecting the expressed polypeptide.

29. The process according to claim 28, wherein the expressing step comprises culturing a host cell transformed with the DNA molecule encoding the polypeptide.

30. The process according to the claim 28, wherein the collecting step comprises one or more techniques selected from the group consisting of salting out, dialysis, filtration, concentration, gel filtration chromatography, affinity chromatography, hydrophobic chromatography, isoelectric focusing and gel electrophoresis.

* * * * *

SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Thr Gly Gly Thr
1

(2) INFORMATION FOR SEQ ID NO: 2:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

His Gly Thr Asp Thr
1               5

(2) INFORMATION FOR SEQ ID NO: 3:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 3:

Gln Cys Leu Xaa Gly
1               5

(2) INFORMATION FOR SEQ ID NO: 4:

(i) SEQUENCE CHARACTERISTICS:
           (A) LENGTH: 363 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 4:

Met Ala Arg Ala Ser Gly Ser Glu Arg His L eu Leu Leu Ile Tyr Thr
1               5                   10                  15

Gly Gly Thr Leu Gly Met Gln Ser Lys Gly G ly Val Leu Val Pro Gly
                20                  25                  30

Pro Gly Leu Val Thr Leu Leu Arg Thr Leu P ro Met Phe His Asp Lys
                35                  40                  45

Glu Phe Ala Gln Ala Gln Gly Leu Pro Asp H is Ala Leu Ala Leu Pro
            50                  55                  60

Pro Ala Ser His Gly Pro Arg Val Leu Tyr T hr Val Leu Glu Cys Gln
65              70                  75                  80

Pro Leu Leu Asp Ser Ser Asp Met Thr Ile A sp Asp Trp Ile Arg Ile
                85                  90                  95

Ala Lys Ile Ile Glu Arg His Tyr Glu Gln T yr Gln Gly Phe Val Val
                100                 105                 110

Ile His Gly Thr Asp Thr Met Ala Phe Gly A la Ser Met Leu Ser Phe
                115                 120                 125

Met Leu Glu Asn Leu His Lys Pro Val Ile L eu Thr Gly Ala Gln Val
            130                 135                 140

Pro Ile Arg Val Leu Trp Asn Asp Ala Arg G lu Asn Leu Leu Gly Ala
145                 150                 155                 160

Leu Leu Val Ala Gly Gln Tyr Ile Ile Pro G lu Val Cys Leu Phe Met
                165                 170                 175

Asn Ser Gln Leu Phe Arg Gly Asn Arg Val T hr Lys Val Asp Ser Gln
                180                 185                 190

Lys Phe Glu Ala Phe Cys Ser Pro Asn Leu S er Pro Leu Ala Thr Val
                195                 200                 205

Gly Ala Asp Val Thr Ile Ala Trp Asp Leu V al Arg Lys Val Asn Trp
                210                 215                 220

```
Lys Asp Pro Leu Val Val His Ser Asn Met Glu His Asp Val Ala Leu
225                 230                 235                 240

Leu Arg Leu Tyr Pro Gly Ile Pro Ala Ser Leu Val Arg Ala Phe Leu
            245                 250                 255

Gln Pro Pro Leu Lys Gly Val Val Leu Glu Thr Phe Gly Ser Gly Asn
            260                 265                 270

Gly Pro Ser Lys Pro Asp Leu Leu Gln Glu Leu Arg Ala Ala Ala Gln
            275                 280                 285

Arg Gly Leu Ile Met Val Asn Cys Ser Gln Cys Leu Arg Gly Ser Val
            290                 295                 300

Thr Pro Gly Tyr Ala Thr Ser Leu Ala Gly Ala Asn Ile Val Ser Gly
305                 310                 315                 320

Leu Asp Met Thr Ser Glu Ala Ala Leu Ala Lys Leu Ser Tyr Val Leu
            325                 330                 335

Gly Leu Pro Glu Leu Ser Leu Glu Arg Arg Gln Glu Leu Leu Ala Lys
            340                 345                 350

Asp Leu Arg Gly Glu Met Thr Leu Pro Thr Ala
            355                 360     363

(2) INFORMATION FOR SEQ ID NO: 5:

(i) SEQUENCE CHARACTERISTICS:
        (A) LENGTH: 565 amino acids
        (B) TYPE: amino acid
        (D) TOPOLOGY: linear (ii) MOLECULE TYPE: peptide (xi) SEQUENCE DESCRIPTION: SEQ ID NO: 5:

Met Ala Arg Ala Ser Gly Ser Glu Arg His Leu Leu Leu Ile Tyr Thr
1               5                   10                  15

Gly Gly Thr Leu Gly Met Gln Ser Lys Gly Gly Val Leu Val Pro Gly
            20                  25                  30

Pro Gly Leu Val Thr Leu Leu Arg Thr Leu Pro Met Phe His Asp Lys
            35                  40                  45

Glu Phe Ala Gln Ala Gln Gly Leu Pro Asp His Ala Leu Ala Leu Pro
    50                  55                  60

Pro Ala Ser His Gly Pro Arg Val Leu Tyr Thr Val Leu Glu Cys Gln
65                  70                  75                  80

Pro Leu Leu Asp Ser Ser Asp Met Thr Ile Asp Asp Trp Ile Arg Ile
            85                  90                  95

Ala Lys Ile Ile Glu Arg His Tyr Glu Gln Tyr Gln Gly Phe Val Val
            100                 105                 110

Ile His Gly Thr Asp Thr Met Ala Phe Gly Ala Ser Met Leu Ser Phe
    115                 120                 125

Met Leu Glu Asn Leu His Lys Pro Val Ile Leu Thr Gly Ala Gln Val
130                 135                 140

Pro Ile Arg Val Leu Trp Asn Asp Ala Arg Glu Asn Leu Leu Gly Ala
145                 150                 155                 160

Leu Leu Val Ala Gly Gln Tyr Ile Ile Pro Glu Val Cys Leu Phe Met
            165                 170                 175

Asn Ser Gln Leu Phe Arg Gly Asn Arg Val Thr Lys Val Asp Ser Gln
            180                 185                 190

Lys Phe Glu Ala Phe Cys Ser Pro Asn Leu Ser Pro Leu Ala Thr Val
    195                 200                 205

Gly Ala Asp Val Thr Ile Ala Trp Asp Leu Val Arg Lys Val Asn Trp
```

```
                  210              215              220
Lys Asp Pro Leu Val Val His Ser Asn Met Glu His Asp Val Ala Leu
225              230              235              240
Leu Arg Leu Tyr Pro Gly Ile Pro Ala Ser Leu Val Arg Ala Phe Leu
                 245              250              255
Gln Pro Pro Leu Lys Gly Val Val Leu Glu Thr Phe Gly Ser Gly Asn
                 260              265              270
Gly Pro Ser Lys Pro Asp Leu Leu Gln Glu Leu Arg Ala Ala Ala Gln
                 275              280              285
Arg Gly Leu Ile Met Val Asn Cys Ser Gln Cys Leu Arg Gly Ser Val
                 290              295              300
Thr Pro Gly Tyr Ala Thr Ser Leu Ala Gly Ala Asn Ile Val Ser Gly
305              310              315              320
Leu Asp Met Thr Ser Glu Ala Ala Leu Ala Lys Leu Ser Tyr Val Leu
                 325              330              335
Gly Leu Pro Glu Leu Ser Leu Glu Arg Arg Gln Glu Leu Leu Ala Lys
                 340              345              350
Asp Leu Arg Gly Glu Met Thr Leu Pro Thr Ala Asp Leu His Gln Ser
                 355              360              365
Ser Pro Pro Gly Ser Thr Leu Gly Gln Gly Val Ala Arg Leu Phe Ser
                 370              375              380
Leu Phe Gly Cys Gln Glu Glu Asp Ser Val Gln Asp Ala Val Met Pro
385              390              395              400
Ser Leu Ala Leu Ala Leu Ala His Ala Gly Glu Leu Glu Ala Leu Gln
                 405              410              415
Ala Leu Met Glu Leu Gly Ser Asp Leu Arg Leu Lys Asp Ser Asn Gly
                 420              425              430
Gln Thr Leu Leu His Val Ala Ala Arg Asn Gly Arg Asp Gly Val Val
                 435              440              445
Thr Met Leu Leu His Arg Gly Met Asp Val Asn Ala Arg Asp Arg Asp
450              455              460
Gly Leu Ser Pro Leu Leu Ala Val Gln Gly Arg His Arg Glu Cys
465              470              475              480
Ile Arg Leu Leu Arg Lys Ala Gly Ala Cys Leu Ser Pro Gln Asp Leu
                 485              490              495
Lys Asp Ala Gly Thr Glu Leu Cys Arg Leu Ala Ser Arg Ala Asp Met
                 500              505              510
Glu Gly Leu Gln Ala Trp Gly Gln Ala Gly Ala Asp Leu Gln Gln Pro
                 515              520              525
Gly Tyr Asp Gly Arg Ser Ala Leu Cys Val Ala Glu Ala Ala Gly Asn
                 530              535              540
Gln Glu Val Leu Ala Leu Leu Arg Asn Leu Ala Leu Val Gly Pro Glu
545              550              555              560
Val Pro Pro Ala Ile
                 565

(2) INFORMATION FOR SEQ ID NO: 6:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO: 6:

```
Met Ala Arg Ala Val Gly Pro Glu Arg Arg Leu Leu Ala Val Tyr Thr
1               5                   10                  15
Gly Gly Thr Ile Gly Met Arg Ser Glu Leu Gly Val Leu Val Pro Gly
                20                  25                  30
Thr Gly Leu Ala Ala Ile Leu Arg Thr Leu Pro Met Phe His Asp Glu
            35                  40                  45
Glu His Ala Arg Ala Arg Gly Leu Ser Glu Asp Thr Leu Val Leu Pro
        50                  55                  60
Pro Asp Ser Arg Asn Gln Arg Ile Leu Tyr Thr Val Leu Glu Cys Gln
65                  70                  75                  80
Pro Leu Phe Asp Ser Ser Asp Met Thr Ile Ala Glu Trp Val Arg Val
                85                  90                  95
Ala Gln Thr Ile Lys Arg His Tyr Glu Gln Tyr His Gly Phe Val Val
                100                 105                 110
Ile His Gly Thr Asp Thr Met Ala Phe Ala Ala Ser Met Leu Ser Phe
            115                 120                 125
Met Leu Glu Asn Leu Gln Lys Thr Val Ile Leu Thr Gly Ala Gln Val
        130                 135                 140
Pro Ile His Ala Leu Trp Ser Asp Gly Arg Glu Asn Leu Leu Gly Ala
145                 150                 155                 160
Leu Leu Met Ala Gly Gln Tyr Val Ile Pro Glu Val Cys Leu Phe Phe
                165                 170                 175
Gln Asn Gln Leu Phe Arg Gly Asn Arg Ala Thr Lys Val Asp Ala Arg
                180                 185                 190
Arg Phe Ala Ala Phe Cys Ser Pro Asn Leu Leu Pro Leu Ala Thr Val
            195                 200                 205
Gly Ala Asp Ile Thr Ile Asn Arg Glu Leu Val Arg Lys Val Asp Gly
        210                 215                 220
Lys Ala Gly Leu Val Val His Ser Ser Met Glu Gln Asp Val Gly Leu
225                 230                 235                 240
Leu Arg Leu Tyr Pro Gly Ile Pro Ala Ala Leu Val Arg Ala Phe Leu
                245                 250                 255
Gln Pro Pro Leu Lys Gly Val Val Met Glu Thr Phe Gly Ser Gly Asn
                260                 265                 270
Gly Pro Thr Lys Pro Asp Leu Leu Gln Glu Leu Arg Val Ala Thr Glu
            275                 280                 285
Arg Gly Leu Val Ile Val Asn Cys Thr Gln Cys Leu Arg Gly Ala Val
        290                 295                 300
Thr Thr Asp Tyr Ala Ala Gly Met Ala Met Ala Gly Ala Asn Val Ile
305                 310                 315                 320
Ser Gly Phe Asp Met Thr Ser Glu Ala Ala Leu Ala Lys Leu Ser Tyr
                325                 330                 335
Val Leu Gly Gln Pro Gly Leu Ser Leu Asp Val Arg Lys Glu Leu Leu
                340                 345                 350
Thr Lys Asp Leu Arg Gly Glu Met Thr Pro Pro Ser Val
            355                 360                 365
```

(2) INFORMATION FOR SEQ ID NO: 7:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
            35                  40                  45

Glu His Ala Arg Ala Arg Gly Leu Ser Glu Asp Thr Leu Val Leu Pro
    50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
                100                 105                 110

Ile His Gly Thr Asp Thr Met Ala Phe Ala Ala Ser Met Leu Ser Phe
        115                 120                 125

Met Leu Glu Asn Leu Gln Lys Thr Val Ile Leu Thr Gly Ala Gln Val
    130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
                180                 185                 190

Arg Phe Ala Ala Phe Cys Ser Pro Asn Leu Leu Pro Leu Ala Thr Val
    195                 200                 205

Gly Ala Asp Ile Thr Ile Asn Arg Glu Leu Val Arg Lys Val Asp Gly
210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
                260                 265                 270

Gly Pro Thr Lys Pro Asp Leu Leu Gln Glu Leu Arg Val Ala Thr Glu
            275                 280                 285

Arg Gly Leu Val Ile Val Asn Cys Thr Gln Cys Leu Arg Gly Ala Val
    290                 295                 300

Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val
355                 360                 365
```

(2) INFORMATION FOR SEQ ID NO: 8:

(i) SEQUENCE CHARACTERISTICS:
        (A) LENGTH: 365 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
                20                  25                  30

Thr Gly Leu Ala Ala Ile Leu Arg Thr Leu Pro Met Phe His Asp Glu
            35                  40                  45

Glu His Ala Arg Ala Arg Gly Leu Ser Glu Asp Thr Leu Val Leu Pro
    50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Thr Val Ile Leu Thr Gly Ala Gln Val
130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
        195                 200                 205

Gly Ala Asp Ile Thr Ile Asn Arg Glu Leu Val Arg Lys Val Asp Gly
210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
        275                 280                 285

Arg Gly Leu Val Ile Val Asn Cys Thr Gln Cys Leu Gln Gly Ala Val
290                 295                 300

Thr Thr Asp Tyr Ala Ala Gly Met Ala Met Ala Gly Ala Asn Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val
        355                 360                 365

(2) INFORMATION FOR SEQ ID NO: 9:

```
    (i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Met Ala Arg Ala Val Gly Pro Glu Arg Arg Leu Leu Ala Val Tyr Thr
1               5                  10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
        35                  40                  45

Glu His Ala Arg Ala Arg Gly Leu Ser Glu Asp Thr Leu Val Leu Pro
    50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Thr Val Ile Leu Thr Gly Ala Gln Val
    130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
        195                 200                 205

Gly Ala Asp Ile Thr Ile Asn Arg Glu Leu Val Arg Lys Val Asp Gly
    210                 215                 220

Lys Ala Gly Leu Val Val His Ser Ser Met Glu Gln Asp Val Gly Leu
225                 230                 235                 240

Leu Arg Leu Tyr Pro Gly Ile Pro Ala Ala Leu Val Arg Ala Phe Leu
                245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
        275                 280                 285

Arg Gly Leu Val Ile Val Asn Cys Thr Gln Cys Leu Gln Gly Ala Val
    290                 295                 300

Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
                325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val
        355                 360                 365
```

(2) INFORMATION FOR SEQ ID NO: 10:

(i) SEQUENCE CHARACTERISTICS:
        (A) LENGTH: 1089 base pairs
        (B) TYPE: nucleic acid
        (C) STRANDEDNESS: single
        (D) TOPOLOGY: linear (xi) SEQUENCE DESCRIPTION: SEQ ID NO: 10:

```
ATGGCGCGCG CATCAGGCTC CGAGAGGCAC CTGCTGCTCA TCTACACTGG C GGCACTTTG      60
GGCATGCAGA GCAAGGGCGG GGTGCTCGTC CCCGGCCCAG GCCTGGTCAC T CTGCTGCGG     120
ACCCTGCCCA TGTTCCATGA CAAGGAGTTC GCCCAGGCCC AGGGCCTCCC T GACCATGCT     180
CTGGCGCTGC CCCCTGCCAG CCACGGCCCC AGGGTCCTCT ACACGGTGCT G GAGTGCCAG     240
CCCCTCTTGG ATTCCAGCGA CATGACCATC GATGATTGGA TTCGCATAGC C AAGATCATA     300
GAGAGGCACT ATGAGCAGTA CCAAGGCTTT GTGGTTATCC ACGGCACCGA C ACCATGGCC     360
TTTGGGGCCT CCATGCTGTC CTTCATGCTG GAAAACCTGC ACAAACCAGT C ATCCTCACT     420
GGCGCCCAGG TGCCAATCCG TGTGCTGTGG AATGACGCCC GGGAAAACCT G CTGGGGGCG     480
TTGCTTGTGG CCGGCCAATA CATCATCCCT GAGGTCTGCC TGTTTATGAA C AGTCAGCTG     540
TTTCGGGGAA ACCGGGTAAC CAAGGTGGAC TCCCAGAAGT TGAGGCCTT C TGCTCCCCC     600
AATCTGTCCC CACTAGCCAC TGTGGGCGCG GATGTCACAA TTGCCTGGGA C CTGGTGCGC     660
AAGGTCAACT GGAAGGACCC GCTGGTGGTG CACAGCAACA TGGAGCACGA C GTGGCACTG     720
CTGCGCCTCT ACCCTGGCAT CCCGGCCTCC CTGGTCCGGG CATTCCTGCA G CCCCCGCTC     780
AAGGGCGTGG TCCTGGAGAC CTTCGGCTCT GGCAACGGGC CGAGCAAGCC C GACCTGCTG     840
CAGGAGTTGC GGGCCGCGGC CCAGCGCGGC CTCATCATGG TCAACTGCAG C CAGTGCCTG     900
CGGGGGTCTG TGACCCCGGG CTATGCCACG AGCTTGGCGG GCGCCAACAT C GTGTCCGGC     960
TTAGACATGA CCTCAGAGGC CGCGCTGGCT AAGCTGTCCT ACGTGTTGGG C CTGCCGGAG    1020
CTGAGCCTGG AGCGCAGGCA GGAGCTGCTG GCCAAGGATC TTCGCGGGGA A ATGACACTG    1080
CCCACGGCA                                                             1089
```

(2) INFORMATION FOR SEQ ID NO: 11:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (xi) SEQUENCE DESCRIPTION: SEQ ID NO: 11:

```
ATGGCGCGCG CGGTGGGGCC CGAGCGGAGG CTGCTGGCCG TCTACACCGG C GGCACCATT      60
GGCATGCGGA GTGAGCTCGG CGTGCTTGTG CCCGGGACGG GCCTGGCTGC C ATCCTGAGG     120
ACACTGCCCA TGTTCCATGA CGAGGAGCAC GCCCGAGCCC GCGGCCTCTC T GAGGACACC     180
CTGGTGCTAC CCCCGGACAG CCGCAACCAG AGGATCCTCT ACACCGTGCT G GAGTGCCAG     240
CCCCTCTTCG ACTCCAGTGA CATGACCATC GCTGAGTGGG TTCGCGTTGC C CAGACCATC     300
AAGAGGCACT ACGAGCAGTA CCACGGCTTT GTGGTCATCC ACGGCACCGA C ACCATGGCC     360
TTTGCTGCCT CGATGCTGTC CTTCATGCTG GAGAACCTGC AGAAGACTGT C ATCCTCACT     420
GGGGCCCAGG TGCCCATCCA TGCCCTGTGG AGCGACGGCC GTGAGAACCT G CTGGGGGCA     480
CTGCTCATGG CTGGCCAGTA TGTGATCCCA GAGGTCTGCC TTTTCTTCCA G AATCAGCTG     540
```

-continued

```
TTTCGGGGCA ACCGGGCAAC CAAGGTAGAC GCTCGGAGGT TCGCAGCTTT C TGCTCCCCG    600

AACCTGCTGC CTCTGGCCAC AGTGGGTGCT GACATCACAA TCAACAGGGA G CTGGTGCGG    660

AAGGTGGACG GGAAGGCTGG GCTGGTGGTG CACAGCAGCA TGGAGCAGGA C GTGGGCCTG    720

CTGCGCCTCT ACCCTGGGAT CCCTGCCGCC CTGGTTCGGG CCTTCTTGCA G CCTCCCCTG    780

AAGGGCGTGG TCATGGAGAC CTTCGGTTCA GGGAACGGAC CCACCAAGCC C GACCTGCTG    840

CAGGAGCTGC GGGTGGCCAC CGAGCGCGGC CTGGTCATCG TCAACTGTAC C CAGTGCCTC    900

CGGGGGGCTG TGACCACAGA CTATGCAGCT GGCATGGCCA TGGCGGGAGC C AACGTCATC    960

TCAGGCTTCG ACATGACATC GGAGGCCGCC CTGGCCAAGC TATCGTATGT G CTGGGCCAG   1020

CCAGGGCTGA GCCTGGATGT CAGGAAGGAG CTGCTGACCA AGGACCTTCG G GGGGAGATG   1080

ACGCCACCCT CGGTG                                                      1095
```

(2) INFORMATION FOR SEQ ID NO: 12:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (xi) SEQUENCE DESCRIPTION: SEQ ID NO: 12:

```
ATGGCGCGCG CGGTGGGGCC CGAGCGGAGG CTGCTGGCCG TCTACACCGG C GGCACCATT     60

GGCATGCGGA GTGAGCTCGG CGTGCTTGTG CCCGGGACGG GCCTGGCTGC C ATCCTGAGG    120

ACACTGCCCA TGTTCCATGA CGAGGAGCAC GCCCGAGCCC GCGGCCTCTC T GAGGACACC    180

CTGGTGCTAC CCCCGGACAG CCGCAACCAG AGGATCCTCT ACACCGTGCT G GAGTGCCAG    240

CCCCTCTTCG ACTCCAGTGA CATGACCATC GCTGAGTGGG TTCGCGTTGC C CAGACCATC    300

AAGAGGCACT ACGAGCAGTA CCACGGCTTT GTGGTCATCC ACGGCACCGA C ACCATGGCC    360

TTTGCTGCCT CGATGCTGTC CTTCATGCTG GAGAACCTGC AGAAGACTGT C ATCCTCACT    420

GGGGCCCAGG TGCCCATCCA TGCCCTGTGG AGCGACGGCC GTGAGAACCT G CTGGGGGCA    480

CTGCTCATGG CTGGCCAGTA TGTGATCCCA GAGGTCTGCC TTTTCTTCCA G AATCAGCTG    540

TTTCGGGGCA ACCGGGCAAC CAAGGTAGAC GCTCGGAGGT TCGCAGCTTT C TGCTCCCCG    600

AACCTGCTGC CTCTGGCCAC AGTGGGTGCT GACATCACAA TCAACAGGGA G CTGGTGCGG    660

AAGGTGGACG GGAAGGCTGG GCTGGTGGTG CACAGCAGCA TGGAGCAGGA C GTGGGCCTG    720

CTGCGCCTCT ACCCTGGGAT CCCTGCCGCC CTGGTTCGGG CCTTCTTGCA G CCTCCCCTG    780

AAGGGCGTGG TCATGGAGAC CTTCGGTTCA GGGAACGGAC CCACCAAGCC C GACCTGCTG    840

CAGGAGCTGC GGGTGGCCAC CGAGCGCGGC CTGGTCATCG TCAACTGTAC C CAGTGCCTC    900

CGGGGGGCTG TGACCACAGA CTATGCAGCT GGCATGGCCA TGGCGGGAGC C GGCGTCATC    960

TCAGGCTTCG ACATGACATC GGAGGCCGCC CTGGCCAAGC TATCGTATGT G CTGGGCCAG   1020

CCAGGGCTGA GCCTGGATGT CAGGAAGGAG CTGCTGACCA AGGACCTTCG G GGGGAGATG   1080

ACGCCACCCT CGGTG                                                      1095
```

(2) INFORMATION FOR SEQ ID NO: 13:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (xi) SEQUENCE DESCRIPTION: SEQ ID NO: 13:

```
ATGGCGCGCG CGGTGGGGCC CGAGCGGAGG CTGCTGGCCG TCTACACCGG C GGCACCATT      60

GGCATGCGGA GTGAGCTCGG CGTGCTTGTG CCCGGGACGG GCCTGGCTGC C ATCCTGAGG     120

ACACTGCCCA TGTTCCATGA CGAGGAGCAC GCCCGAGCCC GCGGCCTCTC T GAGGACACC     180

CTGGTGCTAC CCCCGGACAG CCGCAACCAG AGGATCCTCT ACACCGTGCT G GAGTGCCAG     240

CCCCTCTTCG ACTCCAGTGA CATGACCATC GCTGAGTGGG TTCGCGTTGC C CAGACCATC     300

AAGAGGCACT ACGAGCAGTA CCACGGCTTT GTGGTCATCC ACGGCACCGA C ACCATGGCC     360

TTTGCTGCCT CGATGCTGTC CTTCATGCTG GAGAACCTGC AGAAGACTGT C ATCCTCACT     420

GGGGCCCAGG TGCCCATCCA TGCCCTGTGG AGCGACGGCC GTGAGAACCT G CTGGGGGCA     480

CTGCTCATGG CTGGCCAGTA TGTGATCCCA GAGGTCTGCC TTTTCTTCCA G AATCAGCTG     540

TTTCGGGGCA ACCGGGCAAC CAAGGTAGAC GCTCGGAGGT TCGCAGCTTT C TGCTCCCCG     600

AACCTGCTGC CTCTGGCCAC AGTGGGTGCT GACATCACAA TCAACAGGGA G CTGGTGCGG     660

AAGGTGGACG GGAAGGCTGG GCTGGTGGTG CACAGCAGCA TGGAGCAGGA C GTGGGCCTG     720

CTGCGCCTCT ACCCTGGGAT CCCTGCCGCC CTGGTTCGGG CCTTCTTGCA G CCTCCCCTG     780

AAGGGCGTGG TCATGGAGAC CTTCGGTTCA GGGAACGGAC CCACCAAGCC C GACCTGCTG     840

CAGGAGCTGC GGGTGGCCAC CGAGCGCGGC CTGGTCATCG TCAACTGTAC C CAGTGCCTC     900

CAGGGGGCTG TGACCACAGA CTATGCAGCT GGCATGGCCA TGGCGGGAGC C AACGTCATC     960

TCAGGCTTCG ACATGACATC GGAGGCCGCC CTGGCCAAGC TATCGTATGT G CTGGGCCGC    1020

CCAGGGCTGA GCCTGGATGT CAGGAAGGAG CTGCTGACCA AGGACCTTCG G GGGGAGATG    1080

ACGCCACCCT CGGTG                                                    1095
```

(2) INFORMATION FOR SEQ ID NO: 14:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (xi) SEQUENCE DESCRIPTION: SEQ ID NO: 14:

```
ATGGCGCGCG CGGTGGGGCC CGAGCGGAGG CTGCTGGCCG TCTACACCGG C GGCACCATT      60

GGCATGCGGA GTGAGCTCGG CGTGCTTGTG CCCGGGACGG GCCTGGCTGC C ATCCTGAGG     120

ACACTGCCCA TGTTCCATGA CGAGGAGCAC GCCCGAGCCC GCGGCCTCTC T GAGGACACC     180

CTGGTGCTAC CCCCGGACAG CCGCAACCAG AGGATCCTCT ACACCGTGCT G GAGTGCCAG     240

CCCCTCTTCG ACTCCAGTGA CATGACCATC GCTGAGTGGG TTCGCGTTGC C CAGACCATC     300

AAGAGGCACT ACGAGCAGTA CCACGGCTTT GTGGTCATCC ACGGCACCGA C ACCATGGCC     360

TTTGCTGCCT CGATGCTGTC CTTCATGCTG GAGAACCTGC AGAAGACTGT C ATCCTCACT     420

GGGGCCCAGG TGCCCATCCA TGCCCTGTGG AGCGACGGCC GTGAGAACCT G CTGGGGGCA     480

CTGCTCATGG CTGGCCAGTA TGTGATCCCA GAGGTCTGCC TTTTCTTCCA G AATCAGCTG     540

TTTCGGGGCA ACCGGGCAAC CAAGGTAGAC GCTCGGAGGT TCGCAGCTTT C TGCTCCCCG     600

AACCTGCTGC CTCTGGCCAC AGTGGGTGCT GACATCACAA TCAACAGGGA G CTGGTGCGG     660

AAGGTGGACG GGAAGGCTGG GCTGGTGGTG CACAGCAGCA TGGAGCAGGA C GTGGGCCTG     720

CTGCGCCTCT ACCCTGGGAT CCCTGCCGCC CTGGTTCGGG CCTTCTTGCA G CCTCCCCTG     780

AAGGGCGTGG TCATGGAGAC CTTCGGTTCA GGGAACGGAC CCACCAAGCC C GACCTGCTG     840

CAGGAGCTGC GGGTGGCCAC CGAGCGCGGC CTGGTCATCG TCAACTGTAC C CAGTGCCTC     900
```

-continued

```
CAGGGGGCTG TGACCACAGA CTATGCAGCT GGCATGGCCA TGGCGGGAGC C GGCGTCATC       960

TCAGGCTTCG ACATGACATC GGAGGCCGCC CTGGCCAAGC TATCGTATGT G CTGGGCCAG      1020

CCAGGGCTGA GCCTGGATGT CAGGAAGGAG CTGCTGACCA AGGACCTTCG G GGGGAGATG      1080

ACGCCACCCT CGGTG                                                        1095
```

(2) INFORMATION FOR SEQ ID NO: 15:

(i) SEQUENCE CHARACTERISTICS:
        (A) LENGTH: 1928 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: No (iv) ANTI-SENSE: No (vi) ORIGINAL SOURCE:
        (A) ORGANISM: guinea p ig
        (F) TISSUE TYPE: liver (ix) FEATURE:
        (A) NAME/KEY:mat peptide
        (B) LOCATION:1..19
        (C) IDENTIFICATION METHOD :S (xi) SEQUENCE DESCRIPTION: SEQ ID NO: 15:

```
GAGTGGCTTA GCCGCAGGC ATG GCG CGC GCA TCA GGC TC C GAG AGG CAC            49
                    Met Ala Arg Ala Ser Gly Ser Glu Arg  His
                     1           5                    10

CTG CTG CTC ATC TAC ACT GGC GGC ACT TTG G GC ATG CAG AGC AAG GGC         97
Leu Leu Leu Ile Tyr Thr Gly Gly Thr Leu G ly Met Gln Ser Lys Gly
                 15                  20                  25

GGG GTG CTC GTC CCC GGC CCA GGC CTG GTC A CT CTG CTG CGG ACC CTG        145
Gly Val Leu Val Pro Gly Pro Gly Leu Val T hr Leu Leu Arg Thr Leu
         30                  35                  40

CCC ATG TTC CAT GAC AAG GAG TTC GCC CAG G CC CAG GGC CTC CCT GAC        193
Pro Met Phe His Asp Lys Glu Phe Ala Gln A la Gln Gly Leu Pro Asp
     45                  50                  55

CAT GCT CTG GCG CTG CCC CCT GCC AGC CAC G GC CCC AGG GTC CTC TAC        241
His Ala Leu Ala Leu Pro Pro Ala Ser His G ly Pro Arg Val Leu Tyr
 60                  65                  70

ACG GTG CTG GAG TGC CAG CCC CTC TTG GAT T CC AGC GAC ATG ACC ATC        289
Thr Val Leu Glu Cys Gln Pro Leu Leu Asp S er Ser Asp Met Thr Ile
75                  80                  85                  90

GAT GAT TGG ATT CGC ATA GCC AAG ATC ATA G AG AGG CAC TAT GAG CAG        337
Asp Asp Trp Ile Arg Ile Ala Lys Ile Ile G lu Arg His Tyr Glu Gln
                 95                 100                 105

TAC CAA GGC TTT GTG GTT ATC CAC GGC ACC G AC ACC ATG GCC TTT GGG        385
Tyr Gln Gly Phe Val Val Ile His Gly Thr A sp Thr Met Ala Phe Gly
             110                 115                 120

GCC TCC ATG CTG TCC TTC ATG CTG GAA AAC C TG CAC AAA CCA GTC ATC        433
Ala Ser Met Leu Ser Phe Met Leu Glu Asn L eu His Lys Pro Val Ile
         125                 130                 135

CTC ACT GGC GCC CAG GTG CCA ATC CGT GTG C TG TGG AAT GAC GCC CGG        481
Leu Thr Gly Ala Gln Val Pro Ile Arg Val L eu Trp Asn Asp Ala Arg
     140                 145                 150

GAA AAC CTG CTG GGG GCG TTG CTT GTG GCC G GC CAA TAC ATC ATC CCT        529
Glu Asn Leu Leu Gly Ala Leu Leu Val Ala G ly Gln Tyr Ile Ile Pro
155                 160                 165                 170
```

```
GAG GTC TGC CTG TTT ATG AAC AGT CAG CTG T TT CGG GGA AAC CGG GTA      577
Glu Val Cys Leu Phe Met Asn Ser Gln Leu P he Arg Gly Asn Arg Val
                    175                 180                 185

ACC AAG GTG GAC TCC CAG AAG TTT GAG GCC T TC TGC TCC CCC AAT CTG      625
Thr Lys Val Asp Ser Gln Lys Phe Glu Ala P he Cys Ser Pro Asn Leu
                190                 195                 200

TCC CCA CTA GCC ACT GTG GGC GCG GAT GTC A CA ATT GCC TGG GAC CTG      673
Ser Pro Leu Ala Thr Val Gly Ala Asp Val T hr Ile Ala Trp Asp Leu
                205                 210                 215

GTG CGC AAG GTC AAC TGG AAG GAC CCG CTG G TG GTG CAC AGC AAC ATG      721
Val Arg Lys Val Asn Trp Lys Asp Pro Leu V al Val His Ser Asn Met
220                 225                 230

GAG CAC GAC GTG GCA CTG CTG CGC CTC TAC C CT GGC ATC CCG GCC TCC      769
Glu His Asp Val Ala Leu Leu Arg Leu Tyr P ro Gly Ile Pro Ala Ser
235                 240                 245                 250

CTG GTC CGG GCA TTC CTG CAG CCC CCG CTC A AG GGC GTG GTC CTG GAG      817
Leu Val Arg Ala Phe Leu Gln Pro Pro Leu L ys Gly Val Val Leu Glu
                255                 260                 265

ACC TTC GGC TCT GGC AAC GGG CCG AGC AAG C CC GAC CTG CTG CAG GAG      865
Thr Phe Gly Ser Gly Asn Gly Pro Ser Lys P ro Asp Leu Leu Gln Glu
                270                 275                 280

TTG CGG GCC GCG GCC CAG CGC GGC CTC ATC A TG GTC AAC TGC AGC CAG      913
Leu Arg Ala Ala Ala Gln Arg Gly Leu Ile M et Val Asn Cys Ser Gln
                285                 290                 295

TGC CTG CGG GGG TCT GTG ACC CCG GGC TAT G CC ACG AGC TTG GCG GGC      961
Cys Leu Arg Gly Ser Val Thr Pro Gly Tyr A la Thr Ser Leu Ala Gly
300                 305                 310

GCC AAC ATC GTG TCC GGC TTA GAC ATG ACC T CA GAG GCC GCG CTG GCT     1009
Ala Asn Ile Val Ser Gly Leu Asp Met Thr S er Glu Ala Ala Leu Ala
315                 320                 325                 330

AAG CTG TCC TAC GTG TTG GGC CTG CCG GAG C TG AGC CTG GAG CGC AGG     1057
Lys Leu Ser Tyr Val Leu Gly Leu Pro Glu L eu Ser Leu Glu Arg Arg
                335                 340                 345

CAG GAG CTG CTG GCC AAG GAT CTT CGC GGG G AA ATG ACA CTG CCC ACG     1105
Gln Glu Leu Leu Ala Lys Asp Leu Arg Gly G lu Met Thr Leu Pro Thr
                350                 355                 360

GCA GAC CTG CAC CAG TCC TCT CCG CCG GGC A GC ACA CTG GGG CAA GGT     1153
Ala Asp Leu His Gln Ser Ser Pro Pro Gly S er Thr Leu Gly Gln Gly
                365                 370                 375

GTC GCC CGG CTC TTT AGT CTG TTC GGT TGC C AG GAG GAA GAT TCG GTG     1201
Val Ala Arg Leu Phe Ser Leu Phe Gly Cys G ln Glu Glu Asp Ser Val
                380                 385                 390

CAG GAC GCC GTG ATG CCC AGC CTG GCC CTG G CC TTG GCC CAT GCT GGT     1249
Gln Asp Ala Val Met Pro Ser Leu Ala Leu A la Leu Ala His Ala Gly
395                 400                 405                 410

GAA CTC GAG GCT CTG CAG GCA CTT ATG GAG C TG GGC AGT GAC CTG CGC     1297
Glu Leu Glu Ala Leu Gln Ala Leu Met Glu L eu Gly Ser Asp Leu Arg
                415                 420                 425

CTA AAG GAC TCT AAT GGC CAA ACC CTG TTG C AT GTG GCT GCT CGG AAT     1345
Leu Lys Asp Ser Asn Gly Gln Thr Leu Leu H is Val Ala Ala Arg Asn
                430                 435                 440

GGG CGT GAT GGC GTG GTC ACC ATG CTG CTG C AC AGA GGC ATG GAT GTC     1393
Gly Arg Asp Gly Val Val Thr Met Leu Leu H is Arg Gly Met Asp Val
                445                 450                 455

AAT GCC CGA GAC CGA GAC GGC CTC AGC CCA C TG CTG TTG GCT GTA CAG     1441
Asn Ala Arg Asp Arg Asp Gly Leu Ser Pro L eu Leu Leu Ala Val Gln
            460                 465                 470

GGC AGG CAT CGG GAA TGC ATC AGG CTG CTG C GG AAG GCT GGG GCC TGC     1489
Gly Arg His Arg Glu Cys Ile Arg Leu Leu A rg Lys Ala Gly Ala Cys
475                 480                 485                 490
```

```
CTG TCC CCC CAG GAC CTG AAG GAT GCA GGG A CC GAG CTG TGC AGG CTG        1537
Leu Ser Pro Gln Asp Leu Lys Asp Ala Gly T hr Glu Leu Cys Arg Leu
            495                 500                     505

GCA TCC AGG GCT GAC ATG GAA GGC CTG CAG G CA TGG GGG CAG GCT GGG        1585
Ala Ser Arg Ala Asp Met Glu Gly Leu Gln A la Trp Gly Gln Ala Gly
            510                 515                     520

GCC GAC CTG CAG CAG CCG GGC TAT GAT GGG C GC AGC GCT CTG TGT GTC        1633
Ala Asp Leu Gln Gln Pro Gly Tyr Asp Gly A rg Ser Ala Leu Cys Val
            525                 530                     535

GCA GAA GCA GCC GGG AAC CAG GAG GTG CTG G CC CTT CTG CGG AAC CTG        1681
Ala Glu Ala Ala Gly Asn Gln Glu Val Leu A la Leu Leu Arg Asn Leu
            540                 545                 550

GCA CTT GTA GGC CCG GAA GTG CCG CCT GCC A TC TGATCGCCAG CAATCCCG        1734
Ala Leu Val Gly Pro Glu Val Pro Pro Ala I le
555                 560                 565

GTGGTGTGAG CCACTCCGCC ATCTGCTGCT TTGACCCACT CGAGGGACCC T AGCACACGA      1794

CCCCCCAGCA GGATGCACCC CACTACTTAG AGTATACCCC AGGCTGGCTC A GTGACAAGC      1854

TGCAAAGGTC TTTGTTGGCA GAACAGCAAT AAAGTAACTA CAGAGTGGCC A AAAAAAAAA      1914

AAAAAAAAAA AAAA                                                        1928

(2) INFORMATION FOR SEQ ID NO: 16:

(i) SEQUENCE CHARACTERISTICS:
        (A) LENGTH: 2096 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: No (iv) ANTI-SENSE: No (vi) ORIGINAL SOURCE:
        (A) ORGANISM: human
        (F) TISSUE TYPE: liver (ix) FEATURE:
        (A) NAME/KEY:mat peptide
        (B) LOCATION:1..92
        (C) IDENTIFICATION METHOD :S (xi) SEQUENCE DESCRIPTION: SEQ ID NO: 16:

CGCCCCGGGC CTCCTCCGCG CAGTCCCTGA GTCCCGCAGG CCCTGCGTCC C CGCTGCACA        60

CCCCCGTCCA CTCCCGTGGT CCCCGGTCCG GC ATG GCG CGC GC G GTG GGG CCC         113
                                  Met Ala Arg Ala Val Gly Pro
                                   1               5

GAG CGG AGG CTG CTG GCC GTC TAC ACC GGC G GC ACC ATT GGC ATG CGG         161
Glu Arg Arg Leu Leu Ala Val Tyr Thr Gly G ly Thr Ile Gly Met Arg
            10                  15                  20

AGT GAG CTC GGC GTG CTT GTG CCC GGG ACG G GC CTG GCT GCC ATC CTG         209
Ser Glu Leu Gly Val Leu Val Pro Gly Thr G ly Leu Ala Ala Ile Leu
        25                  30                  35

AGG ACA CTG CCC ATG TTC CAT GAC GAG GAG C AC GCC CGA GCC CGC GGC         257
Arg Thr Leu Pro Met Phe His Asp Glu Glu H is Ala Arg Ala Arg Gly
40                  45                  50                  55

CTC TCT GAG GAC ACC CTG GTG CTA CCC CCG G AC AGC CGC AAC CAG AGG         305
Leu Ser Glu Asp Thr Leu Val Leu Pro Pro A sp Ser Arg Asn Gln Arg
            60                  65                  70

ATC CTC TAC ACC GTG CTG GAG TGC CAG CCC C TC TTC GAC TCC AGT GAC         353
Ile Leu Tyr Thr Val Leu Glu Cys Gln Pro L eu Phe Asp Ser Ser Asp
```

|  |  |  |  |  |  |  |  |  |  |  |  |  |  |  |  |
|---|---|---|---|---|---|---|---|---|---|---|---|---|---|---|---|
|  |  |  | 75 |  |  |  |  | 80 |  |  |  |  | 85 |  |  |
| ATG | ACC | ATC | GCT | GAG | TGG | GTT | CGC | GTT | GCC | C AG | ACC | ATC | AAG | AGG | CAC | 401 |
| Met | Thr | Ile | Ala | Glu | Trp | Val | Arg | Val | Ala | G ln | Thr | Ile | Lys | Arg | His |
|  |  |  | 90 |  |  |  |  | 95 |  |  |  |  | 100 |  |  |

| TAC | GAG | CAG | TAC | CAC | GGC | TTT | GTG | GTC | ATC | C AC | GGC | ACC | GAC | ACC | ATG | 449 |
| Tyr | Glu | Gln | Tyr | His | Gly | Phe | Val | Val | Ile | H is | Gly | Thr | Asp | Thr | Met |
|  |  | 105 |  |  |  |  | 110 |  |  |  |  | 115 |  |  |  |

| GCC | TTT | GCT | GCC | TCG | ATG | CTG | TCC | TTC | ATG | C TG | GAG | AAC | CTG | CAG | AAG | 497 |
| Ala | Phe | Ala | Ala | Ser | Met | Leu | Ser | Phe | Met | L eu | Glu | Asn | Leu | Gln | Lys |
| 120 |  |  |  |  | 125 |  |  |  |  | 130 |  |  |  |  | 135 |  |

| ACT | GTC | ATC | CTC | ACT | GGG | GCC | CAG | GTG | CCC | A TC | CAT | GCC | CTG | TGG | AGC | 545 |
| Thr | Val | Ile | Leu | Thr | Gly | Ala | Gln | Val | Pro | I le | His | Ala | Leu | Trp | Ser |
|  |  |  |  | 140 |  |  |  |  | 145 |  |  |  |  | 150 |  |  |

| GAC | GGC | CGT | GAG | AAC | CTG | CTG | GGG | GCA | CTG | C TC | ATG | GCT | GGC | CAG | TAT | 593 |
| Asp | Gly | Arg | Glu | Asn | Leu | Leu | Gly | Ala | Leu | L eu | Met | Ala | Gly | Gln | Tyr |
|  |  |  |  | 155 |  |  |  |  | 160 |  |  |  |  | 165 |  |  |

| GTG | ATC | CCA | GAG | GTC | TGC | CTT | TTC | TTC | CAG | A AT | CAG | CTG | TTT | CGG | GGC | 641 |
| Val | Ile | Pro | Glu | Val | Cys | Leu | Phe | Phe | Gln | A sn | Gln | Leu | Phe | Arg | Gly |
|  |  |  | 170 |  |  |  |  | 175 |  |  |  |  | 180 |  |  |  |

| AAC | CGG | GCA | ACC | AAG | GTA | GAC | GCT | CGG | AGG | T TC | GCA | GCT | TTC | TGC | TCC | 689 |
| Asn | Arg | Ala | Thr | Lys | Val | Asp | Ala | Arg | Arg | P he | Ala | Ala | Phe | Cys | Ser |
|  |  |  | 185 |  |  |  |  | 190 |  |  |  |  | 195 |  |  |  |

| CCG | AAC | CTG | CTG | CCT | CTG | GCC | ACA | GTG | GGT | G CT | GAC | ATC | ACA | ATC | AAC | 737 |
| Pro | Asn | Leu | Leu | Pro | Leu | Ala | Thr | Val | Gly | A la | Asp | Ile | Thr | Ile | Asn |
| 200 |  |  |  |  | 205 |  |  |  |  | 210 |  |  |  |  | 215 |  |

| AGG | GAG | CTG | GTG | CGG | AAG | GTG | GAC | GGG | AAG | G CT | GGG | CTG | GTG | GTG | CAC | 785 |
| Arg | Glu | Leu | Val | Arg | Lys | Val | Asp | Gly | Lys | A la | Gly | Leu | Val | Val | His |
|  |  |  |  | 220 |  |  |  |  | 225 |  |  |  |  | 230 |  |  |

| AGC | AGC | ATG | GAG | CAG | GAC | GTG | GGC | CTG | CTG | C GC | CTC | TAC | CCT | GGG | ATC | 833 |
| Ser | Ser | Met | Glu | Gln | Asp | Val | Gly | Leu | Leu | A rg | Leu | Tyr | Pro | Gly | Ile |
|  |  |  | 235 |  |  |  |  | 240 |  |  |  |  | 245 |  |  |  |

| CCT | GCC | GCC | CTG | GTT | CGG | GCC | TTC | TTG | CAG | C CT | CCC | CTG | AAG | GGC | GTG | 881 |
| Pro | Ala | Ala | Leu | Val | Arg | Ala | Phe | Leu | Gln | P ro | Pro | Leu | Lys | Gly | Val |
|  |  |  | 250 |  |  |  |  | 255 |  |  |  |  | 260 |  |  |  |

| GTC | ATG | GAG | ACC | TTC | GGT | TCA | GGG | AAC | GGA | C CC | ACC | AAG | CCC | GAC | CTG | 929 |
| Val | Met | Glu | Thr | Phe | Gly | Ser | Gly | Asn | Gly | P ro | Thr | Lys | Pro | Asp | Leu |
|  |  | 265 |  |  |  |  | 270 |  |  |  |  | 275 |  |  |  |  |

| CTG | CAG | GAG | CTG | CGG | GTG | GCC | ACC | GAG | CGC | G GC | CTG | GTC | ATC | GTC | AAC | 977 |
| Leu | Gln | Glu | Leu | Arg | Val | Ala | Thr | Glu | Arg | G ly | Leu | Val | Ile | Val | Asn |
| 280 |  |  |  |  | 285 |  |  |  |  | 290 |  |  |  |  | 295 |  |

| TGT | ACC | CAC | TGC | CTC | CAG | GGG | GCT | GTG | ACC | A CA | GAC | TAT | GCA | GCT | GGC | 1025 |
| Cys | Thr | His | Cys | Leu | Gln | Gly | Ala | Val | Thr | T hr | Asp | Tyr | Ala | Ala | Gly |
|  |  |  | 300 |  |  |  |  | 305 |  |  |  |  | 310 |  |  |  |

| ATG | GCC | ATG | GCG | GGA | GCC | GGC | GTC | ATC | TCA | G GC | TTC | GAC | ATG | ACA | TCG | 1073 |
| Met | Ala | Met | Ala | Gly | Ala | Gly | Val | Ile | Ser | G ly | Phe | Asp | Met | Thr | Ser |
|  |  |  | 315 |  |  |  |  | 320 |  |  |  |  | 325 |  |  |  |

| GAG | GCC | GCC | CTG | GCC | AAG | CTA | TCG | TAT | GTG | C TG | GGC | CAG | CCA | GGG | CTG | 1121 |
| Glu | Ala | Ala | Leu | Ala | Lys | Leu | Ser | Tyr | Val | L eu | Gly | Gln | Pro | Gly | Leu |
|  |  |  | 330 |  |  |  |  | 335 |  |  |  |  | 340 |  |  |  |

| AGC | CTG | GAT | GTC | AGG | AAG | GAG | CTG | CTG | ACC | A AG | GAC | CTT | CGG | GGG | GAG | 1169 |
| Ser | Leu | Asp | Val | Arg | Lys | Glu | Leu | Leu | Thr | L ys | Asp | Leu | Arg | Gly | Glu |
|  |  |  | 345 |  |  |  |  | 350 |  |  |  |  | 355 |  |  |  |

| ATG | ACG | CCA | CCC | TCG | GTG | GAA | GAG | CGC | CGG | C CC | TCA | CTG | CAG | GGC | AAC | 1217 |
| Met | Thr | Pro | Pro | Ser | Val | Glu | Glu | Arg | Arg | P ro | Ser | Leu | Gln | Gly | Asn |
| 360 |  |  |  |  | 365 |  |  |  |  | 370 |  |  |  |  | 375 |  |

| ACG | CTG | GGC | GGT | GGG | GTC | TCC | TGG | CTC | CTC | A GT | CTG | AGC | GGC | AGC | CAG | 1265 |
| Thr | Leu | Gly | Gly | Gly | Val | Ser | Trp | Leu | Leu | S er | Leu | Ser | Gly | Ser | Gln |
|  |  |  |  | 380 |  |  |  |  | 385 |  |  |  |  | 390 |  |  |

| GAG | GCA | GAT | GCC | CTG | CGG | AAT | GCC | CTG | GTG | C CC | AGC | CTG | GCC | TGT | GCT | 1313 |

```
                Glu Ala Asp Ala Leu Arg Asn Ala Leu Val P ro Ser Leu Ala Cys Ala
                        395                 400                 405

GCT GCC CAC GCC GGT GAC GTG GAG GCG CTG C AG GCG CTT GTG GAG CTG        1361
Ala Ala His Ala Gly Asp Val Glu Ala Leu G ln Ala Leu Val Glu Leu
410                 415                     420

GGC AGT GAC CTG GGC CTG GTG GAC TTT AAC G GC CAA ACC CCA CTG CAC        1409
Gly Ser Asp Leu Gly Leu Val Asp Phe Asn G ly Gln Thr Pro Leu His
425                 430                     435

GCG GCC GCC CGG GGA GGC CAC ACA GAG GCA G TC ACC ATG CTG CTG CAG        1457
Ala Ala Ala Arg Gly Gly His Thr Glu Ala V al Thr Met Leu Leu Gln
440                 445                     450                 455

AGA GGT GTG GAC GTG AAC ACC CGG GAC ACG G AT GGC TTC AGC CCG CTG        1505
Arg Gly Val Asp Val Asn Thr Arg Asp Thr A sp Gly Phe Ser Pro Leu
                460                 465                     470

CTG CTG GCC GTG CGG GGC AGG CAT CCG GGT G TC ATT GGG TTG CTG CGG        1553
Leu Leu Ala Val Arg Gly Arg His Pro Gly V al Ile Gly Leu Leu Arg
                475                 480                     485

GAA GCC GGG GCC TCC CTG TCC ACC CAG GAG C TG GAG GAA GCA GGG ACG        1601
Glu Ala Gly Ala Ser Leu Ser Thr Gln Glu L eu Glu Glu Ala Gly Thr
                490                 495                     500

GAG CTG TGC AGG CTG GCA TAC AGG GCC GAC C TC GAA GGC CTG CAG GTG        1649
Glu Leu Cys Arg Leu Ala Tyr Arg Ala Asp L eu Glu Gly Leu Gln Val
505                 510                     515

TGG TGG CAG GCA GGG GCT GAC CTG GGG CAG C CG GGC TAT GAC GGG CAC        1697
Trp Trp Gln Ala Gly Ala Asp Leu Gly Gln P ro Gly Tyr Asp Gly His
520                 525                     530                 535

AGC GCC CTG CAC GTC GCA GAG GCA GCC GGG A AC CTG GCA GTG GTG GCC        1745
Ser Ala Leu His Val Ala Glu Ala Ala Gly A sn Leu Ala Val Val Ala
                540                 545                     550

TTT CTA CAG AGC CTG GAG GGT GCG GTT GGT G CC CAG GCC CCA TGC CCA        1793
Phe Leu Gln Ser Leu Glu Gly Ala Val Gly A la Gln Ala Pro Cys Pro
                555                 560                     565

GAA GTG CTG CCT GGT GTC TAACCTGAAG GCGTCCTGCT G CAGTATAAG              1841
Glu Val Leu Pro Gly Val
        570

CCATTCCTTC CTCCCATGAC CTGCTGGAGG GGTCTCAGGC ATGACCCCAC T CTGGGGCT       1901

GCTTCCCAGC CTGCTCTCAT GTAAAGCCTG AAGGCCTTTG TTGGGCAGGA C GGCAATAAA     1961

GTCTCTGACA TCCCCTCACC AGGTCTGTAC AGCCTGGCTC TGAGAGGCTC T GTCTGGGTC     2021

CGGGACTGTG AAAAAAAAAA AAAAAAAAAA AAAAAAAAAA AAAAAAAAAA A AAAAAAAAA     2081

AAAAAAAAAA AAAAA                                                       2096

(2) INFORMATION FOR SEQ ID NO: 17:

(i) SEQUENCE CHARACTERISTICS:
        (A) LENGTH: 1695 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: No (iv) ANTI-SENSE: No (vi) ORIGINAL SOURCE:
         (A) ORGANISM: guinea p ig
         (F) TISSUE TYPE: liver (ix) FEATURE:
         (A) NAME/KEY:mat peptide
         (B) LOCATION:1..1695
```

(xi) SEQUENCE DESCRIPTION: SEQ ID NO: 17:

```
ATG GCG CGC GCA TCA GGC TCC GAG AGG CAC C TG CTG CTC ATC TAC ACT     48
Met Ala Arg Ala Ser Gly Ser Glu Arg His L eu Leu Leu Ile Tyr Thr
1               5                   10                  15

GGC GGC ACT TTG GGC ATG CAG AGC AAG GGC G GG GTG CTC GTC CCC GGC     96
Gly Gly Thr Leu Gly Met Gln Ser Lys Gly G ly Val Leu Val Pro Gly
            20                  25                  30

CCA GGC CTG GTC ACT CTG CTG CGG ACC CTG C CC ATG TTC CAT GAC AAG    144
Pro Gly Leu Val Thr Leu Leu Arg Thr Leu P ro Met Phe His Asp Lys
        35                  40                  45

GAG TTC GCC CAG GCC CAG GGC CTC CCT GAC C AT GCT CTG GCG CTG CCC    192
Glu Phe Ala Gln Ala Gln Gly Leu Pro Asp H is Ala Leu Ala Leu Pro
50                  55                  60

CCT GCC AGC CAC GGC CCC AGG GTC CTC TAC A CG GTG CTG GAG TGC CAG    240
Pro Ala Ser His Gly Pro Arg Val Leu Tyr T hr Val Leu Glu Cys Gln
65                  70                  75                  80

CCC CTC TTG GAT TCC AGC GAC ATG ACC ATC G AT GAT TGG ATT CGC ATA    288
Pro Leu Leu Asp Ser Ser Asp Met Thr Ile A sp Asp Trp Ile Arg Ile
                85                  90                  95

GCC AAG ATC ATA GAG AGG CAC TAT GAG CAG T AC CAA GGC TTT GTG GTT    336
Ala Lys Ile Ile Glu Arg His Tyr Glu Gln T yr Gln Gly Phe Val Val
            100                 105                 110

ATC CAC GGC ACC GAC ACC ATG GCC TTT GGG G CC TCC ATG CTG TCC TTC    384
Ile His Gly Thr Asp Thr Met Ala Phe Gly A la Ser Met Leu Ser Phe
        115                 120                 125

ATG CTG GAA AAC CTG CAC AAA CCA GTC ATC C TC ACT GGC GCC CAG GTG    432
Met Leu Glu Asn Leu His Lys Pro Val Ile L eu Thr Gly Ala Gln Val
    130                 135                 140

CCA ATC CGT GTG CTG TGG AAT GAC GCC CGG G AA AAC CTG CTG GGG GCG    480
Pro Ile Arg Val Leu Trp Asn Asp Ala Arg G lu Asn Leu Leu Gly Ala
145                 150                 155                 160

TTG CTT GTG GCC GGC CAA TAC ATC ATC CCT G AG GTC TGC CTG TTT ATG    528
Leu Leu Val Ala Gly Gln Tyr Ile Ile Pro G lu Val Cys Leu Phe Met
                165                 170                 175

AAC AGT CAG CTG TTT CGG GGA AAC CGG GTA A CC AAG GTG GAC TCC CAG    576
Asn Ser Gln Leu Phe Arg Gly Asn Arg Val T hr Lys Val Asp Ser Gln
            180                 185                 190

AAG TTT GAG GCC TTC TGC TCC CCC AAT CTG T CC CCA CTA GCC ACT GTG    624
Lys Phe Glu Ala Phe Cys Ser Pro Asn Leu S er Pro Leu Ala Thr Val
        195                 200                 205

GGC GCG GAT GTC ACA ATT GCC TGG GAC CTG G TG CGC AAG GTC AAC TGG    672
Gly Ala Asp Val Thr Ile Ala Trp Asp Leu V al Arg Lys Val Asn Trp
    210                 215                 220

AAG GAC CCG CTG GTG GTG CAC AGC AAC ATG G AG CAC GAC GTG GCA CTG    720
Lys Asp Pro Leu Val Val His Ser Asn Met G lu His Asp Val Ala Leu
225                 230                 235                 240

CTG CGC CTC TAC CCT GGC ATC CCG GCC TCC C TG GTC CGG GCA TTC CTG    768
Leu Arg Leu Tyr Pro Gly Ile Pro Ala Ser L eu Val Arg Ala Phe Leu
                245                 250                 255

CAG CCC CCG CTC AAG GGC GTG GTC CTG GAG A CC TTC GGC TCT GGC AAC    816
Gln Pro Pro Leu Lys Gly Val Val Leu Glu T hr Phe Gly Ser Gly Asn
            260                 265                 270

GGG CCG AGC AAG CCC GAC CTG CTG CAG GAG T TG CGG GCC GCG GCC CAG    864
Gly Pro Ser Lys Pro Asp Leu Leu Gln Glu L eu Arg Ala Ala Ala Gln
        275                 280                 285

CGC GGC CTC ATC ATG GTC AAC TGC AGC CAG T GC CTG CGG GGG TCT GTG    912
Arg Gly Leu Ile Met Val Asn Cys Ser Gln C ys Leu Arg Gly Ser Val
    290                 295                 300
```

```
ACC CCG GGC TAT GCC ACG AGC TTG GCG GGC G CC AAC ATC GTG TCC GGC         960
Thr Pro Gly Tyr Ala Thr Ser Leu Ala Gly A la Asn Ile Val Ser Gly
305                 310                 315                 320

TTA GAC ATG ACC TCA GAG GCC GCG CTG GCT A AG CTG TCC TAC GTG TTG        1008
Leu Asp Met Thr Ser Glu Ala Ala Leu Ala L ys Leu Ser Tyr Val Leu
                325                 330                 335

GGC CTG CCG GAG CTG AGC CTG GAG CGC AGG C AG GAG CTG CTG GCC AAG        1056
Gly Leu Pro Glu Leu Ser Leu Glu Arg Arg G ln Glu Leu Leu Ala Lys
            340                 345                 350

GAT CTT CGC GGG GAA ATG ACA CTG CCC ACG G CA GAC CTG CAC CAG TCC        1104
Asp Leu Arg Gly Glu Met Thr Leu Pro Thr A la Asp Leu His Gln Ser
        355                 360                 365

TCT CCG CCG GGC AGC ACA CTG GGG CAA GGT G TC GCC CGG CTC TTT AGT        1152
Ser Pro Pro Gly Ser Thr Leu Gly Gln Gly V al Ala Arg Leu Phe Ser
    370                 375                 380

CTG TTC GGT TGC CAG GAG GAA GAT TCG GTG C AG GAC GCC GTG ATG CCC        1200
Leu Phe Gly Cys Gln Glu Glu Asp Ser Val G ln Asp Ala Val Met Pro
385                 390                 395                 400

AGC CTG GCC CTG GCC TTG GCC CAT GCT GGT G AA CTC GAG GCT CTG CAG        1248
Ser Leu Ala Leu Ala Leu Ala His Ala Gly G lu Leu Glu Ala Leu Gln
                405                 410                 415

GCA CTT ATG GAG CTG GGC AGT GAC CTG CGC C TA AAG GAC TCT AAT GGC        1296
Ala Leu Met Glu Leu Gly Ser Asp Leu Arg L eu Lys Asp Ser Asn Gly
                420                 425                 430

CAA ACC CTG TTG CAT GTG GCT GCT CGG AAT G GG CGT GAT GGC GTG GTC        1344
Gln Thr Leu Leu His Val Ala Ala Arg Asn G ly Arg Asp Gly Val Val
            435                 440                 445

ACC ATG CTG CTG CAC AGA GGC ATG GAT GTC A AT GCC CGA GAC CGA GAC        1392
Thr Met Leu Leu His Arg Gly Met Asp Val A sn Ala Arg Asp Arg Asp
        450                 455                 460

GGC CTC AGC CCA CTG CTG TTG GCT GTA CAG G GC AGG CAT CGG GAA TGC        1440
Gly Leu Ser Pro Leu Leu Leu Ala Val Gln G ly Arg His Arg Glu Cys
465                 470                 475                 480

ATC AGG CTG CTG CGG AAG GCT GGG GCC TGC C TG TCC CCC CAG GAC CTG        1488
Ile Arg Leu Leu Arg Lys Ala Gly Ala Cys L eu Ser Pro Gln Asp Leu
                485                 490                 495

AAG GAT GCA GGG ACC GAG CTG TGC AGG CTG G CA TCC AGG GCT GAC ATG        1536
Lys Asp Ala Gly Thr Glu Leu Cys Arg Leu A la Ser Arg Ala Asp Met
                500                 505                 510

GAA GGC CTG CAG GCA TGG GGG CAG GCT GGG G CC GAC CTG CAG CAG CCG        1584
Glu Gly Leu Gln Ala Trp Gly Gln Ala Gly A la Asp Leu Gln Gln Pro
            515                 520                 525

GGC TAT GAT GGG CGC AGC GCT CTG TGT GTC G CA GAA GCA GCC GGG AAC        1632
Gly Tyr Asp Gly Arg Ser Ala Leu Cys Val A la Glu Ala Ala Gly Asn
        530                 535                 540

CAG GAG GTG CTG GCC CTT CTG CGG AAC CTG G CA CTT GTA GGC CCG GAA        1680
Gln Glu Val Leu Ala Leu Leu Arg Asn Leu A la Leu Val Gly Pro Glu
    545                 550                 555                 560

GTG CCG CCT GCC ATC                                                     1695
Val Pro Pro Ala Ile
                565
```

(2) INFORMATION FOR SEQ ID NO: 18:

(i) SEQUENCE CHARACTERISTICS:
        (A) LENGTH: 1719 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: No (iv) ANTI-SENSE: No (vi) ORIGINAL SOURCE:
              (A) ORGANISM: human
              (F) TISSUE TYPE: liver (ix) FEATURE:
              (A) NAME/KEY:mat peptide
              (B) LOCATION:1..1719

(xi) SEQUENCE DESCRIPTION: SEQ ID NO: 18:

```
ATG GCG CGC GCG GTG GGG CCC GAG CGG AGG C TG CTG GCC GTC TAC ACC         48
Met Ala Arg Ala Val Gly Pro Glu Arg Arg L eu Leu Ala Val Tyr Thr
 1               5                  10                  15

GGC GGC ACC ATT GGC ATG CGG AGT GAG CTC G GC GTG CTT GTG CCC GGG         96
Gly Gly Thr Ile Gly Met Arg Ser Glu Leu G ly Val Leu Val Pro Gly
                20                  25                  30

ACG GGC CTG GCT GCC ATC CTG AGG ACA CTG C CC ATG TTC CAT GAC GAG        144
Thr Gly Leu Ala Ala Ile Leu Arg Thr Leu P ro Met Phe His Asp Glu
            35                  40                  45

GAG CAC GCC CGA GCC CGC GGC CTC TCT GAG G AC ACC CTG GTG CTA CCC        192
Glu His Ala Arg Ala Arg Gly Leu Ser Glu A sp Thr Leu Val Leu Pro
        50                  55                  60

CCG GAC AGC CGC AAC CAG AGG ATC CTC TAC A CC GTG CTG GAG TGC CAG        240
Pro Asp Ser Arg Asn Gln Arg Ile Leu Tyr T hr Val Leu Glu Cys Gln
 65                 70                  75                  80

CCC CTC TTC GAC TCC AGT GAC ATG ACC ATC G CT GAG TGG GTT CGC GTT        288
Pro Leu Phe Asp Ser Ser Asp Met Thr Ile A la Glu Trp Val Arg Val
                85                  90                  95

GCC CAG ACC ATC AAG AGG CAC TAC GAG CAG T AC CAC GGC TTT GTG GTC        336
Ala Gln Thr Ile Lys Arg His Tyr Glu Gln T yr His Gly Phe Val Val
               100                 105                 110

ATC CAC GGC ACC GAC ACC ATG GCC TTT GCT G CC TCG ATG CTG TCC TTC        384
Ile His Gly Thr Asp Thr Met Ala Phe Ala A la Ser Met Leu Ser Phe
           115                 120                 125

ATG CTG GAG AAC CTG CAG AAG ACT GTC ATC C TC ACT GGG GCC CAG GTG        432
Met Leu Glu Asn Leu Gln Lys Thr Val Ile L eu Thr Gly Ala Gln Val
       130                 135                 140

CCC ATC CAT GCC CTG TGG AGC GAC GGC CGT G AG AAC CTG CTG GGG GCA        480
Pro Ile His Ala Leu Trp Ser Asp Gly Arg G lu Asn Leu Leu Gly Ala
145                 150                 155                 160

CTG CTC ATG GCT GGC CAG TAT GTG ATC CCA G AG GTC TGC CTT TTC TTC        528
Leu Leu Met Ala Gly Gln Tyr Val Ile Pro G lu Val Cys Leu Phe Phe
               165                 170                 175

CAG AAT CAG CTG TTT CGG GGC AAC CGG GCA A CC AAG GTA GAC GCT CGG        576
Gln Asn Gln Leu Phe Arg Gly Asn Arg Ala T hr Lys Val Asp Ala Arg
               180                 185                 190

AGG TTC GCA GCT TTC TGC TCC CCG AAC CTG C TG CCT CTG GCC ACA GTG        624
Arg Phe Ala Ala Phe Cys Ser Pro Asn Leu L eu Pro Leu Ala Thr Val
           195                 200                 205

GGT GCT GAC ATC ACA ATC AAC AGG GAG CTG G TG CGG AAG GTG GAC GGG        672
Gly Ala Asp Ile Thr Ile Asn Arg Glu Leu V al Arg Lys Val Asp Gly
       210                 215                 220

AAG GCT GGG CTG GTG GTG CAC AGC AGC ATG G AG CAG GAC GTG GGC CTG        720
Lys Ala Gly Leu Val Val His Ser Ser Met G lu Gln Asp Val Gly Leu
225                 230                 235                 240

CTG CGC CTC TAC CCT GGG ATC CCT GCC GCC C TG GTT CGG GCC TTC TTG        768
Leu Arg Leu Tyr Pro Gly Ile Pro Ala Ala L eu Val Arg Ala Phe Leu
               245                 250                 255

CAG CCT CCC CTG AAG GGC GTG GTC ATG GAG A CC TTC GGT TCA GGG AAC        816
```

```
                                                        -continued

Gln Pro Pro Leu Lys Gly Val Val Met Glu T hr Phe Gly Ser Gly Asn
        260                 265             270

GGA CCC ACC AAG CCC GAC CTG CTG CAG GAG C TG CGG GTG GCC ACC GAG      864
Gly Pro Thr Lys Pro Asp Leu Leu Gln Glu L eu Arg Val Ala Thr Glu
        275                 280             285

CGC GGC CTG GTC ATC GTC AAC TGT ACC CAC T GC CTC CAG GGG GCT GTG      912
Arg Gly Leu Val Ile Val Asn Cys Thr His C ys Leu Gln Gly Ala Val
        290                 295             300

ACC ACA GAC TAT GCA GCT GGC ATG GCC ATG G CG GGA GCC GGC GTC ATC      960
Thr Thr Asp Tyr Ala Ala Gly Met Ala Met A la Gly Ala Gly Val Ile
305             310             315                     320

TCA GGC TTC GAC ATG ACA TCG GAG GCC GCC C TG GCC AAG CTA TCG TAT     1008
Ser Gly Phe Asp Met Thr Ser Glu Ala Ala L eu Ala Lys Leu Ser Tyr
                325             330              335

GTG CTG GGC CAG CCA GGG CTG AGC CTG GAT G TC AGG AAG GAG CTG CTG     1056
Val Leu Gly Gln Pro Gly Leu Ser Leu Asp V al Arg Lys Glu Leu Leu
        340             345              350

ACC AAG GAC CTT CGG GGG GAG ATG ACG CCA C CC TCG GTG GAA GAG CGC     1104
Thr Lys Asp Leu Arg Gly Glu Met Thr Pro P ro Ser Val Glu Glu Arg
        355             360              365

CGG CCC TCA CTG CAG GGC AAC ACG CTG GGC G GT GGG GTC TCC TGG CTC     1152
Arg Pro Ser Leu Gln Gly Asn Thr Leu Gly G ly Gly Val Ser Trp Leu
        370             375              380

CTC AGT CTG AGC GGC AGC CAG GAG GCA GAT G CC CTG CGG AAT GCC CTG     1200
Leu Ser Leu Ser Gly Ser Gln Glu Ala Asp A la Leu Arg Asn Ala Leu
385             390             395                      400

GTG CCC AGC CTG GCC TGT GCT GCT GCC CAC G CC GGT GAC GTG GAG GCG     1248
Val Pro Ser Leu Ala Cys Ala Ala Ala His A la Gly Asp Val Glu Ala
                405             410              415

CTG CAG GCG CTT GTG GAG CTG GGC AGT GAC C TG GGC CTG GTG GAC TTT     1296
Leu Gln Ala Leu Val Glu Leu Gly Ser Asp L eu Gly Leu Val Asp Phe
        420             425              430

AAC GGC CAA ACC CCA CTG CAC GCG GCC GCC C GG GGA GGC CAC ACA GAG     1344
Asn Gly Gln Thr Pro Leu His Ala Ala Ala A rg Gly Gly His Thr Glu
        435             440              445

GCA GTC ACC ATG CTG CTG CAG AGA GGT GTG G AC GTG AAC ACC CGG GAC     1392
Ala Val Thr Met Leu Leu Gln Arg Gly Val A sp Val Asn Thr Arg Asp
        450             455              460

ACG GAT GGC TTC AGC CCG CTG CTG CTG GCC G TG CGG GGC AGG CAT CCG     1440
Thr Asp Gly Phe Ser Pro Leu Leu Leu Ala V al Arg Gly Arg His Pro
465             470             475                      480

GGT GTC ATT GGG TTG CTG CGG GAA GCC GGG G CC TCC CTG TCC ACC CAG     1488
Gly Val Ile Gly Leu Leu Arg Glu Ala Gly A la Ser Leu Ser Thr Gln
                485             490              495

GAG CTG GAG GAA GCA GGG ACG GAG CTG TGC A GG CTG GCA TAC AGG GCC     1536
Glu Leu Glu Glu Ala Gly Thr Glu Leu Cys A rg Leu Ala Tyr Arg Ala
        500             505              510

GAC CTC GAA GGC CTG CAG GTG TGG TGG CAG G CA GGG GCT GAC CTG GGG     1584
Asp Leu Glu Gly Leu Gln Val Trp Trp Gln A la Gly Ala Asp Leu Gly
        515             520              525

CAG CCG GGC TAT GAC GGG CAC AGC GCC CTG C AC GTC GCA GAG GCA GCC     1632
Gln Pro Gly Tyr Asp Gly His Ser Ala Leu H is Val Ala Glu Ala Ala
        530             535              540

GGG AAC CTG GCA GTG GTG GCC TTT CTA CAG A GC CTG GAG GGT GCG GTT     1680
Gly Asn Leu Ala Val Val Ala Phe Leu Gln S er Leu Glu Gly Ala Val
545             550             555                      560

GGT GCC CAG GCC CCA TGC CCA GAA GTG CTG C CT GGT GTC                 1719
Gly Ala Gln Ala Pro Cys Pro Glu Val Leu P ro Gly Val
                565             570        573
```

(2) INFORMATION FOR SEQ ID NO: 19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

AATCTCGAGC CACCATGGCG CGCGCATCA                                    29

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

CTGCGGCCGC TTATCAGATG GCAGGCGGCA C                                31

(2) INFORMATION FOR SEQ ID NO: 21:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Gly Ser Gly Asn Gly Pro Thr Lys Pro Asp L eu Leu Gln Glu Leu Arg
1             5                   10                15

Cys (2) INFORMATION FOR SEQ ID NO: 22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

AATCTCGAGC CACCATGGCG CGCGCGGTG                                    29

(2) INFORMATION FOR SEQ ID NO: 23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

CTGCGGCCGC TTATCAGACA CCAGGCAGCA C                                31

(2) INFORMATION FOR SEQ ID NO: 24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

CTGCGGCCGC TTATCATGCC GTGGGCAGTG T                          31

(2) INFORMATION FOR SEQ ID NO: 25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

CTGCGGCCGC TTATCAGCCC AACACGTAGG A                          31

(2) INFORMATION FOR SEQ ID NO: 26:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

CTGCGGCCGC TCATTACACC GAGGGTGGCG T                          31

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

CCCCCGGAGG CACTGGGT                                         18

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

ACCCAGTGCC TCCGGGGG                                         18

(2) INFORMATION FOR SEQ ID NO: 29:

(i) SEQUENCE CHARACTERISTICS:
        (A) LENGTH: 18 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 29:

CCCCTGGAGG CACTGGGT                                                 18

(2) INFORMATION FOR SEQ ID NO: 30:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 30:

ACCCAGTGCC TCCAGGGG                                                 18

(2) INFORMATION FOR SEQ ID NO: 31:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 31:

CCCCCGGAGG CAGTGGGT                                                 18

(2) INFORMATION FOR SEQ ID NO: 32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 32:

ACCCACTGCC TCCGGGGG                                                 18

(2) INFORMATION FOR SEQ ID NO: 33:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 33:

GACGTTGGCT CCCGCCAT                                                 18

(2) INFORMATION FOR SEQ ID NO: 34:

(i) SEQUENCE CHARACTERISTICS:
            (A) LENGTH: 18 base pairs
            (B) TYPE: nucleic acid
            (C) STRANDEDNESS: single
            (D) TOPOLOGY: linear

```
       (ii) MOLECULE TYPE: cDNA (xi) SEQUENCE DESCRIPTION: SEQ ID NO: 34:

ATGGCGGGAG CCAACGTC                                                    18

(2) INFORMATION FOR SEQ ID NO: 35:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 35:

GCGAATTCAT GGCGCGCGCA TCA                                              23

(2) INFORMATION FOR SEQ ID NO: 36:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 36:

GCAAGCTTTC AGATGGCAGG CGGCAC                                           26

(2) INFORMATION FOR SEQ ID NO: 37:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 37:

GTGAATTCGG AGGTTCAGAT GGCGCGCGCA TCA                                   33

(2) INFORMATION FOR SEQ ID NO: 38:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 38:

CTGCGGCCGC TCAGATGGCA GGCGGCAC                                         28

(2) INFORMATION FOR SEQ ID NO: 39:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 39:
```

TCGAGCCACC ATGAAGTGTT CGTGGGTTAT T                                31

(2) INFORMATION FOR SEQ ID NO: 40:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

TTCTTCCTGA TGGCCGTAGT GACAGGAGTG                                  30

(2) INFORMATION FOR SEQ ID NO: 41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

AATTCACTCC TGTCACTACG GCCATCAGGA                                  30

(2) INFORMATION FOR SEQ ID NO: 42:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 42:

AGAAAATAAC CCACGAACAC TTCATGGTGG C                                31

(2) INFORMATION FOR SEQ ID NO: 43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

GCAAGCTTTC ATGCCGTGGG CAGTGT                                      26

(2) INFORMATION FOR SEQ ID NO: 44:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

GCGAATTCAT GGCGCGCGCG GTG                                         23

(2) INFORMATION FOR SEQ ID NO: 45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 45:

GCAAGCTTTC ACACCGAGGG TGGCGT                                              26

(2) INFORMATION FOR SEQ ID NO: 46:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

CTGCGGCCGC TCATGCCGTG GGCAGTG                                             27

(2) INFORMATION FOR SEQ ID NO: 47:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

CTGAATTCGG AGGTTCAGAT GGCGCGCGCG GGTG                                     34

(2) INFORMATION FOR SEQ ID NO: 48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

CTGCGGCCGC TCACACCGAG GTGGCG                                              27

(2) INFORMATION FOR SEQ ID NO: 49:

(i) SEQUENCE CHARACTERISTICS:
        (A) LENGTH: 565 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Met Ala Arg Ala Ser Gly Ser Glu Arg His L eu Leu Leu Ile Tyr Thr
 1               5                  10                  15

Gly Gly Thr Leu Gly Met Gln Ser Lys Gly G ly Val Leu Val Pro Gly
                20                  25                  30

Pro Gly Leu Val Thr Leu Leu Arg Thr Leu P ro Met Phe His Asp Lys
                35                  40                  45

```
Glu Phe Ala Gln Ala Gln Gly Leu Pro Asp His Ala Leu Ala Leu Pro
 50                  55                  60
Pro Ala Ser His Gly Pro Arg Val Leu Tyr Thr Val Leu Glu Cys Gln
 65                  70                  75                  80
Pro Leu Leu Asp Ser Ser Asp Met Thr Ile Asp Asp Trp Ile Arg Ile
                 85                  90                  95
Ala Lys Ile Ile Glu Arg His Tyr Glu Gln Tyr Gln Gly Phe Val Val
                100                 105                 110
Ile His Gly Thr Asp Thr Met Ala Phe Gly Ala Ser Met Leu Ser Phe
            115                 120                 125
Met Leu Glu Asn Leu His Lys Pro Val Ile Leu Thr Gly Ala Gln Val
130                 135                 140
Pro Ile Arg Val Leu Trp Asn Asp Ala Arg Glu Asn Leu Leu Gly Ala
145                 150                 155                 160
Leu Leu Val Ala Gly Gln Tyr Ile Ile Pro Glu Val Cys Leu Phe Met
                165                 170                 175
Asn Ser Gln Leu Phe Arg Gly Asn Arg Val Thr Lys Val Asp Ser Gln
                180                 185                 190
Lys Phe Glu Ala Phe Cys Ser Pro Asn Leu Ser Pro Leu Ala Thr Val
            195                 200                 205
Gly Ala Asp Val Thr Ile Ala Trp Asp Leu Val Arg Lys Val Asn Trp
210                 215                 220
Lys Asp Pro Leu Val Val His Ser Asn Met Glu His Asp Val Ala Leu
225                 230                 235                 240
Leu Arg Leu Tyr Pro Gly Ile Pro Ala Ser Leu Val Arg Ala Phe Leu
                245                 250                 255
Gln Pro Pro Leu Lys Gly Val Val Leu Glu Thr Phe Gly Ser Gly Asn
                260                 265                 270
Gly Pro Ser Lys Pro Asp Leu Leu Gln Glu Leu Arg Ala Ala Ala Gln
            275                 280                 285
Arg Gly Leu Ile Met Val Asn Cys Ser Gln Cys Leu Arg Gly Ser Val
290                 295                 300
Thr Pro Gly Tyr Ala Thr Ser Leu Ala Gly Ala Asn Ile Val Ser Gly
305                 310                 315                 320
Leu Asp Met Thr Ser Glu Ala Ala Leu Ala Lys Leu Ser Tyr Val Leu
                325                 330                 335
Gly Leu Pro Glu Leu Ser Leu Glu Arg Arg Gln Glu Leu Leu Ala Lys
                340                 345                 350
Asp Leu Arg Gly Glu Met Thr Leu Pro Thr Ala Asp Leu His Gln Ser
            355                 360                 365
Ser Pro Pro Gly Ser Thr Leu Gly Gln Gly Val Ala Arg Leu Phe Ser
370                 375                 380
Leu Phe Gly Cys Gln Glu Glu Asp Ser Val Gln Asp Ala Val Met Pro
385                 390                 395                 400
Ser Leu Ala Leu Ala Leu Ala His Ala Gly Glu Leu Glu Ala Leu Gln
                405                 410                 415
Ala Leu Met Glu Leu Gly Ser Asp Leu Arg Leu Lys Asp Ser Asn Gly
                420                 425                 430
Gln Thr Leu Leu His Val Ala Ala Arg Asn Gly Arg Asp Gly Val Val
            435                 440                 445
Thr Met Leu Leu His Arg Gly Met Asp Val Asn Ala Arg Asp Arg Asp
450                 455                 460
```

-continued

```
Gly Leu Ser Pro Leu Leu Leu Ala Val Gln Gly Arg His Arg Glu Cys
465                 470                 475                 480

Ile Arg Leu Leu Arg Lys Ala Gly Ala Cys Leu Ser Pro Gln Asp Leu
                485                 490                 495

Lys Asp Ala Gly Thr Glu Leu Cys Arg Leu Ala Ser Arg Ala Asp Met
            500                 505                 510

Glu Gly Leu Gln Ala Trp Gly Gln Ala Gly Ala Asp Leu Gln Gln Pro
        515                 520                 525

Gly Tyr Asp Gly Arg Ser Ala Leu Cys Val Ala Glu Ala Ala Gly Asn
    530                 535                 540

Gln Glu Val Leu Ala Leu Leu Arg Asn Leu Ala Leu Val Gly Pro Glu
545                 550                 555                 560

Val Pro Pro Ala Ile
            565
```

(2) INFORMATION FOR SEQ ID NO: 50:

(i) SEQUENCE CHARACTERISTICS:
        (A) LENGTH: 573 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

```
Met Ala Arg Ala Val Gly Pro Glu Arg Arg Leu Leu Ala Val Tyr Thr
1               5                   10                  15

Gly Gly Thr Ile Gly Met Arg Ser Glu Leu Gly Val Leu Val Pro Gly
            20                  25                  30

Thr Gly Leu Ala Ala Ile Leu Arg Thr Leu Pro Met Phe His Asp Glu
        35                  40                  45

Glu His Ala Arg Ala Arg Gly Leu Ser Glu Asp Thr Leu Val Leu Pro
    50                  55                  60

Pro Asp Ser Arg Asn Gln Arg Ile Leu Tyr Thr Val Leu Glu Cys Gln
65                  70                  75                  80

Pro Leu Phe Asp Ser Ser Asp Met Thr Ile Ala Glu Trp Val Arg Val
                85                  90                  95

Ala Gln Thr Ile Lys Arg His Tyr Glu Gln Tyr His Gly Phe Val Val
            100                 105                 110

Ile His Gly Thr Asp Thr Met Ala Phe Ala Ala Ser Met Leu Ser Phe
        115                 120                 125

Met Leu Glu Asn Leu Gln Lys Thr Val Ile Leu Thr Gly Ala Gln Val
130                 135                 140

Pro Ile His Ala Leu Trp Ser Asp Gly Arg Glu Asn Leu Leu Gly Ala
145                 150                 155                 160

Leu Leu Met Ala Gly Gln Tyr Val Ile Pro Glu Val Cys Leu Phe Phe
                165                 170                 175

Gln Asn Gln Leu Phe Arg Gly Asn Arg Ala Thr Lys Val Asp Ala Arg
            180                 185                 190

Arg Phe Ala Ala Phe Cys Ser Pro Asn Leu Leu Pro Leu Ala Thr Val
        195                 200                 205

Gly Ala Asp Ile Thr Ile Asn Arg Glu Leu Val Arg Lys Val Asp Gly
    210                 215                 220

Lys Ala Gly Leu Val Val His Ser Ser Met Glu Gln Asp Val Gly Leu
225                 230                 235                 240
```

-continued

```
Leu Arg Leu Tyr Pro Gly Ile Pro Ala Ala Leu Val Arg Ala Phe Leu
            245                 250                 255

Gln Pro Pro Leu Lys Gly Val Val Met Glu Thr Phe Gly Ser Gly Asn
            260                 265                 270

Gly Pro Thr Lys Pro Asp Leu Leu Gln Glu Leu Arg Val Ala Thr Glu
            275                 280                 285

Arg Gly Leu Val Ile Val Asn Cys Thr His Cys Leu Gln Gly Ala Val
            290                 295                 300

Thr Thr Asp Tyr Ala Ala Gly Met Ala Met Ala Gly Ala Gly Val Ile
305                 310                 315                 320

Ser Gly Phe Asp Met Thr Ser Glu Ala Ala Leu Ala Lys Leu Ser Tyr
            325                 330                 335

Val Leu Gly Gln Pro Gly Leu Ser Leu Asp Val Arg Lys Glu Leu Leu
            340                 345                 350

Thr Lys Asp Leu Arg Gly Glu Met Thr Pro Pro Ser Val Glu Glu Arg
            355                 360                 365

Arg Pro Ser Leu Gln Gly Asn Thr Leu Gly Gly Gly Val Ser Trp Leu
            370                 375                 380

Leu Ser Leu Ser Gly Ser Gln Glu Ala Asp Ala Leu Arg Asn Ala Leu
385                 390                 395                 400

Val Pro Ser Leu Ala Cys Ala Ala Ala His Ala Gly Asp Val Glu Ala
            405                 410                 415

Leu Gln Ala Leu Val Glu Leu Gly Ser Asp Leu Gly Leu Val Asp Phe
            420                 425                 430

Asn Gly Gln Thr Pro Leu His Ala Ala Ala Arg Gly Gly His Thr Glu
            435                 440                 445

Ala Val Thr Met Leu Leu Gln Arg Gly Val Asp Val Asn Thr Arg Asp
450                 455                 460

Thr Asp Gly Phe Ser Pro Leu Leu Leu Ala Val Arg Gly Arg His Pro
465                 470                 475                 480

Gly Val Ile Gly Leu Leu Arg Glu Ala Gly Ala Ser Leu Ser Thr Gln
            485                 490                 495

Glu Leu Glu Glu Ala Gly Thr Glu Leu Cys Arg Leu Ala Tyr Arg Ala
            500                 505                 510

Asp Leu Glu Gly Leu Gln Val Trp Trp Gln Ala Gly Ala Asp Leu Gly
            515                 520                 525

Gln Pro Gly Tyr Asp Gly His Ser Ala Leu His Val Ala Glu Ala Ala
            530                 535                 540

Gly Asn Leu Ala Val Val Ala Phe Leu Gln Ser Leu Glu Gly Ala Val
545                 550                 555                 560

Gly Ala Gln Ala Pro Cys Pro Glu Val Leu Pro Gly Val
            565                 570         573
```